United States Patent
Maroy et al.

(10) Patent No.: US 7,630,550 B2
(45) Date of Patent: Dec. 8, 2009

(54) METHOD OF SEGMENTATION OF A SEQUENCE OF THREE-DIMENSIONAL IMAGES, IN PARTICULAR IN PHARMACO-IMAGERIE

(75) Inventors: Renaud Maroy, Paris (FR); Bertrand Tavitian, Paris (FR); Vincent Frouin, Villemoisson sur Orge (FR)

(73) Assignee: Commissariat a l'Energie Atomique, Paris (FR)

(*) Notice: Subject to any disclaimer, the term of this patent is extended or adjusted under 35 U.S.C. 154(b) by 715 days.

(21) Appl. No.: 11/335,712

(22) Filed: Jan. 20, 2006

(65) Prior Publication Data

US 2006/0269130 A1 Nov. 30, 2006

(30) Foreign Application Priority Data

May 30, 2005 (FR) ................................. 05 05441

(51) Int. Cl.
*G06K 9/34* (2006.01)
(52) U.S. Cl. .................. 382/173; 382/171; 382/190
(58) Field of Classification Search ............... 382/173, 382/171, 101, 190, 159, 128, 131, 154; 375/240.1, 375/E7.091, E7.018; 209/584; 600/445, 600/443, 512, 509
See application file for complete search history.

(56) References Cited

U.S. PATENT DOCUMENTS 6,389,310 B1 * 5/2002 Demonceau et al. ........ 600/512
6,934,405 B1 * 8/2005 Schuessler .................. 382/101
7,302,001 B2 * 11/2007 Wang et al. ............... 375/240.1

FOREIGN PATENT DOCUMENTS

EP 1365356 A2 11/2003

OTHER PUBLICATIONS

J. Ashburner, et al., "A Cluster Analysis Approach for the Characterization of Dynamic PET Data", Quantification of Brain Function Using PET, Copyright 1996 by Academic Press, pp. 301-306.

(Continued)

*Primary Examiner*—Anh Hong Do
(74) *Attorney, Agent, or Firm*—Clark & Brody

(57) ABSTRACT

The present invention relates to a method of segmenting a starting image or sequence of tridimensional images for obtaining a tridimensional segmentation image comprising a partition into regions of interest, said image or sequence of images comprising measurements, for each voxel and in the course of n time intervals ($n \geq 1$), of the real evolution of a signal representative of at least one variable of said image or sequence, which comprises essentially:
  a) a modeling (10) of the signal comprising the definition of a parametric model of spatio-temporal evolution of said signal, this model comprising sets of homogeneous parameters respectively specific to structures corresponding to said regions of interest;
  b) an extraction (30) of samples of voxels respectively included in said structures; then
  c) a merging (50*b*) of the samples grouping together those whose evolution model is specific to the same structure, said merging following, preceding or including a classification of all the voxels of said image or sequence of images or of a zone of interest of the latter by aggregation with a group of samples.

25 Claims, 10 Drawing Sheets

OTHER PUBLICATIONS

P. Acton, et al., "Automatic segmentation of dynamic neuroreceptor single-photon emission tomography images using fuzzy clustering", European Journal of Nuclear Medicine, vol. 26, No. 26, Jun. 1999, pp. 581-590.

J. Brankov, et al., "Segmentation of Dynamic PET or fMRI Images Based on a Similarity Metric", IEEE Transactions on Nuclear Science, vol. 50, No. 5, Oct. 2003, pp. 1410-1414.

H. Guo, et al., "Clustering huge data sets for parametric PET imaging", BioSystems 71 (2003) pp. 81-92.

F. Frouin, et al., "3D Regularisation and Segmentation of Factor Volumes to Process PET $H_2^{15}O$ Myocardial Perfusion Studies", Lecture Notes in Computer Sciences 2230, pp. 91-96, 2001.

V. Frouin, et al., "Correction of Partial-Volume Effect for PET Striatal Imaging: Fast Implementation and Study of Robustness", The Journal of Nuclear Medicine, vol. 43, No. 12, pp. 1715-1726, 2002.

A. Jain, et al., "Algorithms for Clustering Data", Advanced Reference, Prentice Hall, Englewood Cliffs, NJ, 1988.

Y. Kimura, et al., "Fast formation of statistically reliable FDG parametric images based on clustering and principal components", Physics in Medicine and Biology vol. 47 (2002), pp. 455-468.

J.F. Mangin, et al., "Robust Brain Segmentation Using Histogram Scale-Space Analysis and Mathematical Morphology", Lecture Notes in Computer Sciences 1496, pp. 1230-1241, 1998.

T. Minka, "Automatic choice of dimensionality for PCA", M.I.T. Media Laboratory Perceptual Computing Section Technical Report No. 514, pp. 1-16, Dec. 2000.

T. Nichols, et al., "Spatiotemporal Reconstruction of List-Mode PET Data", IEEE Transactions on Medical Imaging, vol. 21, No. 4, Apr. 2002, pp. 396-404.

W. Segars, et al., "Development of a 4D Digital Mouse Phantom for Molecular Imaging Research", Molecular Imaging and Biology, 2004.

M. Tipping, et al., "Mixtures of Probabilistic Principal Component Anaylsers", Neural Computation 11(2), 1999, pp. 443-482.

K. Wong, et al., "Segmentation of Dynamic PET Images Using Cluster Analysis", IEEE Transactions on Nuclear Science, vol. 49, No. 1, Feb. 2002, pp. 200-207.

Y. Zhou, et al., "Linear regression with spatial constraint to generate parametric images of ligand-receptor dynamic PET studies with a simplified reference tissue model", NeuroImage 18 (2003), pp. 975-989.

F. O'Sullivan, "Imaging Radiotracer Model Parameters in PET: A Mixture Analysis Approach", IEEE Transactions on Medical Imaging, vol. 12, No. 3, Sep. 1993, pp. 399-412.

F. Frouin, et al., "Global Strategy to Extract Automatically Relevant Subdominant Perfusion Information: Application to Skeletal Muscle NMR Imaging with Arterial Spin Labeling", Proceedings IEEE International Symposium on Jul. 7, 2002, pp. 569-572.

* cited by examiner

— Bladder tissular kinetic
-- Bladder non physiological kinetics family
···· Muscle tissular kinetic

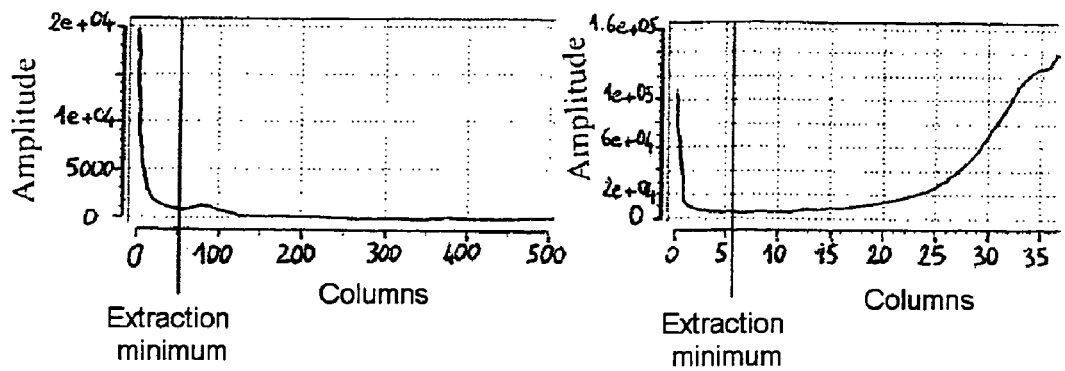
Fig. 6a  Fig. 6b
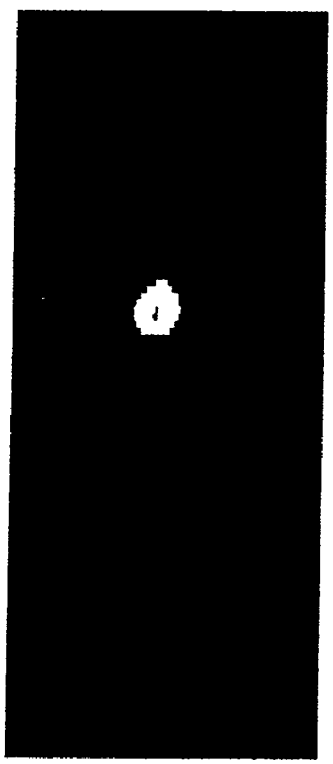 
Fig. 7a  Fig. 7b

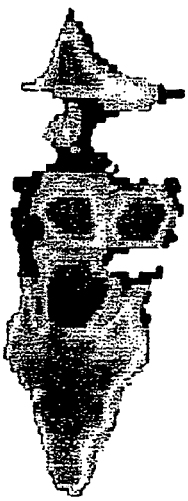 
Fig. 8a  Fig. 8b
 
Fig. 9a  Fig. 9b

METHOD OF SEGMENTATION OF A SEQUENCE OF THREE-DIMENSIONAL IMAGES, IN PARTICULAR IN PHARMACO-IMAGERIE

FIELD OF THE INVENTION

The present invention relates to a method of segmenting an image or a sequence of tridimensional images into a tridimensional image partitioned into regions of interest. The invention applies in a general manner to all types of images, in particular in the fields of pharmaco-imaging and satellite imaging. It applies also to bidimensional images, which are particular cases of tridimensional images in which the value of one of the dimensions is equal to unity.

BACKGROUND ART

A recent and notable evolution in the development of medicines is the use of pharmaco-imaging to measure pharmacokinetic parameters. In a known manner, pharmacokinetics is the component of pharmacology which describes the disposition of medicines in the organism, and specifies in a qualitative and quantitative manner the processes of absorption, distribution, metabolization and elimination of an active principle.

The great advantage of pharmaco-imaging as compared with conventional techniques, which require the repeated extraction of biological samples, is its ability to measure the concentration of the active principle in the organs of the human patient or live animal. One thus avoids the need to sacrifice batches of animals, and one substantially decreases the dispersion of values—all the measurements of the kinetics being made in the same animal. Moreover, the kinetics can be analyzed in the deep organs in man.

On the other hand, pharmaco-imaging requires an implementation which may be technologically unwieldy: firstly marking, radioactive or other, of the active principle to be tracked; next, proof that the detection by imaging does indeed give a quantitative measure of the concentration of the active principle; finally, the tagging of the anatomical location of the signal related to the marked active principle.

In a general but not exclusive manner, a preferred technique of pharmaco-imaging is positon emission tomography (PET) which, on account of the principle of detection on which it is based, is among the imaging techniques best suited to quantitative measurements of molecular concentrations in human or animal organs.

In any event, the measurement of the concentration of a marked active principle (hereinafter called a tracer) at a point of the organism studied is only interpretable from the pharmacokinetic standpoint if it is possible to assign this point to a defined organ, either on an anatomical basis, or on a physiological basis: the heart, the liver, the kidney, a tumor, a region of the brain, etc. However, the image is solely representative of the location of the indicator (radioactive positon emitter in the case of PET) related to the active principle studied, and does not contain a priori any anatomical or physiological information, but solely pharmacokinetic information. It is therefore necessary to superimpose the successive images of location of the tracer on one or more images providing clues about the anatomy and/or physiology. This superposition or registration may be done in several ways:

In the most favorable and least frequent case, the distribution of the tracer discloses a recognizable anatomy. This is the case for tracers that concentrate in the whole of a notable anatomical system such as the skeleton, which do not require additional registration, all the information being in the image. Conversely, this is also the case for certain tracers which diffuse very well in all organs (for example fluorodeoxyglucose). In the latter case, the organs are delimited on the images by a contrast dependent on the level of retention of the tracer, this not necessarily being sufficient for their identification, for example in the case of two adjoining organs having the same tracer retention level. In a general manner, this case where registration is of little or no use relates only to "generalist" tracers (ions, metabolic precursors etc.) and not to the imaging of active principles.

In numerous other cases, the organs are tagged by "overlaying" of an anatomic image emanating from the examiner's knowledge about pharmaco-images. A biologist may often guess the location of anatomical organs, such as the liver or the heart, on the images whose contrast scale tracks the dynamics of the concentration of the tracer. The accuracy of location obtained then depends on the ability to identify the organ, hence on the distribution of the tracer which to a greater or lesser extent delimits the contours of an organ, and on the skill or experience of the examiner. It is understood that this method without anatomical image is inapplicable to the case of a tracer which is present at just one point.

Increasingly often, the examiner calls upon a second image which he superimposes on the pharmaco-image, via a second mode of imaging in which the contrast is not based on location of the tracer but on anatomy (for example tomodensitometry, or magnetic resonance imaging or MRI which is applied to the same individual, preferably during the same imaging session. By superimposing the two images, the pharmaco-image is registered on an anatomical image which identifies the organs. This dual modality is being increasingly widely used for clinical imaging with the recent advent of the "PET-CT" system associating PET camera and X-ray tomodensitometer. However, the dual modality is not totally satisfactory for pharmaco-imaging for both fundamental and practical reasons:

From the fundamental standpoint, the anatomical image merely overlays static information on the pharmacokinetic information given by the pharmaco-image. The link, other than the subject, between the anatomical image and the pharmaco-image can therefore be established only if the pharmacokinetic location of the tracer exactly tracks the organ contours described by the anatomical image. Consequently, the additional information afforded by the anatomical image is limited to the resolution of the anatomical imaging method used, which is far from always being sufficient to identify the nature of all pharmaco-organs. For example, tomodensitometry affords little contrast in soft tissues and the brain, MRI distinguishes pulmonary masses poorly, etc.

From the practical standpoint:

Coupled cameras of "PET-CT" type are currently available only for man, hence with a large aperture and a lower resolution than PET cameras dedicated to small animals. These cameras are necessarily more expensive than PET cameras alone.

In the case of anatomical imaging by tomodensitometry, the irradiation dose required to obtain an image in a small rodent is far from being negligible. This poses problems of toxicity and/or of interpretation of results in the case of the imaging of tumors.

The registration quality obtained is contingent on the total immobility of the subject throughout the duration of the pharmacokinetics explored, this not being the case when transporting an animal from one camera to another.

Additionally, the pharmacokinetic interpretation of PET images generally requires the delimitation of regions of interest ("ROI") representative of the organs. Kimura and coll. [Kimura, 2002] and Zhou [Zhou, 2003] have shown that a suitable grouping of volume elements (voxels) improves the quality of the pharmacokinetic quantification. Specifically, the tracing of the regions of interest presupposes that each organ or part of an organ exhibits homogeneous behavior in respect of a given tracer, which may be characterized by physiological kinetics. Consequently, whatever the method of segmentation, the outlines of the organs traced must be visible in order to prevent the regions of interest from encompassing two organs or parts of organs with different functions (called pharmaco-organs hereinafter). The quality of the segmentation of the image into regions of interest that are consistent from the pharmacokinetic standpoint is therefore crucial. However, the regions of interest are in general traced manually, this being a lengthy and irksome job dependent on the operator and requiring a certain degree of expertise.

A certain number of works, whose aim was not limited to the pharmacokinetic analysis of images, have proposed methods of automatic segmentation making it possible to dispense with the operator for the segmentation of the regions of interest. PET images suffer from a low signal-to-noise ratio. Since they also suffer from low spatial resolution, the activity measured at a given volume element of the image is polluted by the activity contained in the neighboring volume elements. In particular, the measurement of the concentration of the tracer in the organs of small size may either be underestimated, or overestimated depending on whether the radioactive concentration in the surrounding structures is higher or lower. This so-called "partial volume" effect may in fact be modeled as a smoothing of the image [Frouin, 2002] and therefore renders the contours of the organs intrinsically fuzzy. As a consequence, the parts of the organs near the boundaries of the latter will not contain the kinetics of a single pharmaco-organ, but a linear combination of the kinetics of all the nearby pharmaco-organs. Thus, the kinetics of the pharmaco-organ most represented within a volume element is not necessarily that of the pharmaco-organ(s) actually contained in this volume element.

Furthermore, dynamic PET images represent in a known manner a large mass of data (some half a million kinetics), the processing of which is prohibitive in terms of calculation time and computer memory required [Guo, 2003]. In the images, the organism studied represents between 20% and 40% of the data. The remaining part, outside the organism, contains mainly noise.

It is known moreover that the kinetics within a volume element (this term designates the elementary volume unit of the image) is meaningful only on condition that the pharmaco-organ studied is perfectly immobile during the image sequence acquisition time. Any motion of the pharmaco-organ imaged breaks the link between the kinetics of a volume element and the kinetics of this pharmaco-organ. Physiological motions, which are extremely difficult to correct, are of two kinds.

Certain motions are periodic, with a period that is generally less than the duration of acquisition of an image of the sequence. Heart beats and respiration impose a displacement of the neighboring organs, generating a blurring effect which is not negligible, but almost constant from one acquisition to the next.

Other non periodic motions are unpredictable, such as the movement of the viscera during digestion and under the effect of respiration, or the filling of the bladder during the examination: the apparent volume of the bladder may increase tenfold between the start and the end of the examination. For tracers excreted in the urine, the concentration of the tracer and of the metabolites in the urine becomes very high. A voxel corresponding to a visceral or muscular region at the start of the examination may therefore contain a kinetic characteristic of the bladder at the end of the examination. As shown in FIG. 2 attached, the filling of the bladder generates a family of kinetics composed for the early acquisition times of the kinetics of a pharmaco-organ near to the bladder, and for the later times of the kinetics of the bladder. The hypothesis of a fixed number of kinetics contained in a PET image, to within noise and the partial volume effect, does not therefore apply in the case of an imaged organism subject to non periodic physiological motions.

Finally, it is known that the noise in PET images differs according to the methods of reconstructing images used.

Within an image arising from an analytical reconstruction by filtered retroprojection, the noise is often considered to be stationary Gaussian additive in the image, and uncorrelated with the signal. On the other hand, the noise of an image of the sequence depends on the duration of acquisition of this image. This dependency may be considered to be linear [Guo, 2003] with respect to the inverse of the duration of acquisition of the image.

In the images arising from iterative statistical methods, such as "OSEM" ("Ordered Subset Expectation Maximization", method reconstructing the image by maximizing the likelihood of its projection according to various angles of incidence) or "AWOSEM" ("Attenuation Weighted Ordered Subset Expectation Maximization", method operating in a similar manner to "OSEM" by taking into account the phenomenon of attenuation of the photons by the organism), it is no longer possible to assume stationary noise in space. The noise depends on the number of iterations used for the reconstruction, stationary phenomenon, but is also correlated with the signal. We can write: $\sigma^2 = \alpha^2 \times S$, where $\sigma$ represents the local variance of the noise at a given instance, $\alpha$ a constant independent of position and time, but dependent on the method of reconstruction used and on the number of iterations chosen, and S the signal at the point considered. In this particular case, the signal-to-noise ratio is expressed as $S/\sigma = \alpha \times S^{1/2}$. The separation of the noise and of the signal at any point of the image allows the calculation of $\alpha$ and makes it possible to finely characterize the noise. As in the case of reconstruction by an analytic method, the data should be corrected for the influence of the duration of acquisition of each image of the sequence.

Several methods of segmenting PET images into aggregates grouping together zones with homogeneous kinetics, without a prior anatomical knowledge, have recently been proposed in order to attempt to solve the aforementioned problems.

Ashburner [Ashburner, 1996] assumes that a PET image contains a known number of kinetics—one per aggregate—, and therefore describes any kinetic of a voxel of the image as the kinetic of an aggregate, multiplied by a scale factor, to which is added multinormal Gaussian noise—with a normal law for each image acquired—identical for each aggregate.

Wong and coll. [Wong, 2002] assume the kinetics to be homogeneous within one and the same aggregate, but dissimilar between different aggregates. They propose an aggregation approach by the k-means method, which maximizes the variance of the kinetics between the classes, while minimizing the variance of the kinetics within one and the same class. The kinetic of an aggregate is then estimated as the mean of the kinetics of the individuals of which it is composed.

Frouin F. and coll. [Frouin, 2001] also use the k-means method to produce a segmentation of the heart on perfusion images. However, the aggregation is not done on the kinetics themselves, but on factors extracted from the kinetics by factorial analysis, ensuring better robustness of the segmentation. However, the interpretation of the factors of a factorial analysis becomes difficult beyond 4 or 5 factors, thus excluding its direct use on a whole body. It will be noted that the method described by Frouin F. and coll does not segment an organism into pharmaco-organs, but a pharmaco-organ into zones of preeminence of factors such as the arterial, veinous and tissular kinetics.

Acton [Acton, 1999] uses the method of fuzzy c-means, much like k-means, but allowing better account to be taken of the intrinsically fuzzy nature of the data acquired in tomography by simple photons, while ensuring better robustness.

Kimura and coll. [Kimura, 2002] propose a method of aggregation over the projections of the kinetics onto the eigenvectors associated with the two largest eigenvalues of a principal component analysis performed on the whole set of kinetics of the organism, so as to extract compartmental modeling parameters.

Brankov and coll. [Brankov, 2003] propose a use of a similarity measure defined as the cosine of the angle formed between two vectors represented in the kinetics space, rather than a Euclidian norm or a total variance norm. This similarity measure exhibits strong sensitivity to noise in zones of low signal-to-noise ratio. Brankov and coll. present two algorithms of expectation-maximization type ("EM"), one fuzzy and the other binary, which determine aggregates within which the individuals—kinetics—exhibit strong similarity. The "EM" methodology makes it possible to iteratively estimate a hidden variable whose image is a particular realization conforming to a chosen model. Each iteration comprises a first expectation phase in which the expected likelihood of the complete data is calculated on the basis of the joint distribution of the observed and hidden data, and a second maximization phase in which the parameters of the model which maximizes this expected likelihood of the model are estimated. The process is repeated until the algorithm converges.

Brankov compares his method in particular with an application of mixtures of probabilistic principal component analyzers. This method, introduced by Tipping and Bishop [Tipping, 1999], models the signal within the zone to be segmented by a mixture of projections onto subspaces of the space of kinetics.

A major drawback of all these methods is that they are randomly initialized. At each run, the algorithm converges to one of its local minima. However, the solution sought corresponds a priori to the global minimum of this energy. Several runs of the program with different initializations each time are therefore necessary in order to approach the best solution.

Guo [Guo, 2003] proposes an aggregation by hierarchical ascending classification making it possible to obtain a number of aggregates that is defined a posteriori, but also to retain the aggregates of small size. For the calculation of the distance between kinetics, the value at the volume elements considered is weighted at each instant of the kinetic by the signal-to-noise ratio expected for the corresponding image. This ratio, for a given image of the sequence, is assumed to depend essentially on the duration of acquisition of this image. The hierarchical approach ensures the convergence of the algorithm to an optimal minimum, but at the price of a calculation time that does not allow the whole of the data volume to be examined. Moreover, any voxel merging obtained by this algorithm is definitive. Consequently, erroneous assignment of a voxel during the first few iterations, for example on account of noise, cannot be corrected during successive iterations.

Guo and coll. [Guo, 2003] propose a histogram-based pre-segmentation in order to obtain first groupings accelerating a hierarchical ascending classification. The latter operates by a succession of merges of individuals in an optimal order according to a chosen criterion. The two individuals—typically voxels of the image—that are closest in terms of a chosen distance are aggregated, then the aggregates or closest individuals are again aggregated, and so on and so forth until a stopping criterion is satisfied or else until there exists only one aggregate grouping together all the individuals. The histogram used by Guo and coll. can be described as a counting of the number of voxels having a given intensity. This histogram-based classification employs the values of the last image in the temporal sense of the series acquired after administration of the tracer. It is assumed that the first few merges have little impact on the final aggregates and the voxels corresponding to the same interval of the histogram of the last image of the sequence are grouped together. The variation in the spatial distribution is assumed to be minimal for this last image from among all those contained in the time interval considered, the tracer having had maximum time to disperse in the organs according to its affinity. However, in the case of the isotopes with short radioactive period used in PET, on account of the exponential decay of the radioactivity over time, this entails the drawback of increased noise because the last series also exhibits the lowest signal-to-noise ratio of all the images of the series.

Out of all these methods, only that of F. Frouin is validated on moving organs with small-period periodic type motions. However, on account of the principle thereof, it is applicable only to zones of the organism comprising very few pharmaco-organs. None of the other aforementioned methods has been validated in the case of a whole body problem area, and none are suitable for physiological motions specific to this problem area.

The patent document EP-A-1 365 356 presents a method of semi-automatic segmentation of images acquired by PET, which requires in particular the prior delineation of a region of interest and of model-voxels to be extracted from the images. It will be noted that the method presented in this latter document is limited to the field of oncology and that it does not enable the images to be segmented into as many regions of interest as pharmaco-organs, but only into two parts just one of which contains a tumor.

SUMMARY OF THE INVENTION

An aim of the present invention is to propose a method of segmenting a starting image or sequence of tridimensional images based on voxels for obtaining a tridimensional segmentation image comprising a partition into regions of interest, said image or sequence of images comprising measurements, for each voxel and in the course of n time intervals ($n \geq 1$), of the real evolution of a signal representative of at least one variable of physical, chemical or biological type of said image or sequence which makes it possible to remedy these drawbacks.

For this purpose, the method of segmentation according to the invention essentially comprises the following steps:

a) a modeling of the signal comprising the definition of a parametric model of spatio-temporal evolution of said signal, this model comprising sets of homogeneous parameters so that said sets are respectively specific to structures corresponding to said regions of interest and that each set of parameters is independent of the spatial coordinates in the corresponding structure (these parameters will be said to be "homogeneous" hereinafter);

b) an extraction of samples of voxels so that said samples are respectively included in said structures, this extraction comprising:

(i) a calculation, for each voxel of said starting image or sequence of images or else of a zone of interest of the latter, of a criterion of validity of a hypothesis according to which said model of evolution of said variable within the neighborhood of this voxel is specific to one and only one of said structures, (ii) an extraction of model-voxels which are defined as realizing the local maxima of said criterion, (iii) a definition, for each model-voxel, of one of said samples of voxels included in said corresponding structure, in such a way that this sample exhibits an evolution of said variable which complies with that of the model of the structure to which said model-voxel belongs, then (iv) an estimation, on each sample thus defined, of the parameters of said model of evolution of the structure in which said sample is included; then c) a merging of said samples grouping together the samples whose evolution model is specific to the same structure, said merging following, preceding or including a classification of all the voxels of said image or sequence of images or of a zone of interest of the latter by aggregation with a group of samples, in such a manner that a maximum similarity exists between the evolution of said variable for these voxels and the evolution of said model characterizing this group of samples.

This invention applies equally well to bidimensional images, which may be particular cases of tridimensional images in which one of the three dimensions adopts the value one. As indicated hereinabove, we use the term "tridimensional" to designate bidimensional images, which are a particular case of tridimensional images, and also tridimensional images.

It is essential to note that the method according to the invention allows automatic segmentation into structures or regions of interest (e.g. pharmaco-organs), which is based solely on the information (e.g. pharmacokinetic) present in a sequential series of images, in particular by virtue of the non random initialization that it comprises in the aforesaid step b) in which the parameters of the models of the structures of interest are extracted in zones positioned automatically within these models. This initialization is tailored to the data to be processed. This method thus makes it possible to systematically obtain the same result on one and the same data set with the same parameters, on account of its deterministic nature.

The term "voxel" is understood in the present description to mean a unit element, generally chosen to be cubic, of the "3D" volume image. It is the smallest spatial volume available within the image. Pixels are elements of bidimensional images and may be considered to be particular cases of voxels. Hereinbelow, we shall use the term "voxel" to encompass the terms "voxel" and "pixel".

The term "region" is understood to mean a connected zone of the image, i.e. a single piece. Two regions will be said to be connected if they are touching.

Preferably, said image or sequence of images is obtained by an imaging technique chosen from the group consisting of positon emission tomography (PET), magnetic resonance imaging (MRI), photon emission tomography (e.g. "SPECT"), optical imagings, X-ray scanner, histological imaging, autoradiographic imaging, satellite imaging and photographic imaging.

In a general manner, it will be noted that the imaging technique used may equally well be of "2D" or "3D" type.

Still more preferentially, said sequence of images is obtained by the PET technique. In this case, local principal component analyses in a space with n dimensions are advantageously implemented in step b), either in the neighborhood of a voxel, or at a sample, so as, on the one hand, to calculate the criterion of validity of the hypothesis according to which said model of evolution within the neighborhood of said voxel is specific to a single structure and, on the other hand, to estimate on the basis of a sample the parameters of the model of evolution of the structure in which this sample is included.

A principal component analysis (PCA) operated on such a set of multidimensional measurements comprises a change of reference frame, such that a minimum of axes can account for a maximum of the variance of the signal. We distinguish between the eigenvectors or direction vectors of the axes picked up by the PCA, and the eigenvalues which are respectively associated with these axes and which each represent the variance of the signal along the corresponding axis. In general, the axes or eigenvectors are sorted by decreasing eigenvalue.

The reconstruction of a measurement is represented by the first k eigenvectors of the PCA, and this measurement is projected onto the subspace determined by the k eigenvectors associated with the largest k eigenvalues of the PCA. The residual of the projection is equal to the measurement itself from which is subtracted the projection of this measurement onto the PCA, and this residual, representative of the noise relating to the measurements, corresponds to a projection onto the axes of small variance.

The variance of the non reconstructed signal within the set of measurements is equal to the mean of the smallest eigenvalues of the PCA that are not taken into account in the reconstruction of the signal. If the number of eigenvalues employed is just sufficient to reconstruct the signal within the set, the variance of the non reconstructed signal represents the variance of the noise. If this number of eigenvalues is too small, the variance of the non reconstructed signal will contain both noise and signal.

Moreover, the signal-related variance of the non reconstructed signal is defined as follows. If we divide the standard deviation of the non reconstructed signal by the norm of the mean of the signal within the set, we obtain the signal-to-noise ratio when k is just large enough for the first k eigenvectors of the PCA to reconstruct the signal. In a zone with no signal, although the variance of the non reconstructed signal will be identical to what it would be in a zone in which the signal is properly reconstructed, the signal-related variance of the non reconstructed signal will be too large.

We also define the proportion of non reconstructed signal as being equal to the norm of the reconstruction residual for the measurement by the PCA, divided by the norm of this same measurement.

In its particularly advantageous application to pharmaco-imaging, it will be noted that the method according to the invention meets the requirements of whole-body imaging. Specifically, said starting images may advantageously be images of a human or animal whole organism, the segmentation image segmenting said body into a partition of pharmaco-organs whose respective contours delimit the regions of interest.

In this application, it will also be noted that the method according to the invention meets moreover the requirements of moving whole-body imaging, insofar as this method is applicable to a whole organism imbued with physiological motions of periodic type such as respiration and heart beat, whose period is reduced in comparison with the duration of acquisition of one of the starting images of said sequence, or indeed to non periodic physiological motions.

Thus, a kinetic of concentrations may consist of a mixture of pharmaco-organs which will have passed through the volume element where this kinetic is read. The kinetic read at a given instant will contain the same ratio of each pharmaco-organ as the same kinetic at another instant. Moreover, the model chosen in step a) makes it possible to take account of periodic motions of this type during the step of extracting the model-voxels, excluding the image zones traversed by several pharmaco-organs in the course of the periodic motion.

As regards non periodic motions or those whose period is of the order of the duration of acquisition of an image of the sequence (e.g. digestion, dilation of the bladder, overall motion of the body), no model-voxel may be extracted in the zones affected by such motions, because the kinetics of none of these zones can locally satisfy the model with a single organ. These zones will therefore be excluded from the critical phase of determining the models of the pharmaco-organs (see FIG. 2 which illustrates kinetics relating to non periodic motions of bladders of rats).

It will be noted that the present invention makes it possible to dispense with the limitation imposed by a purely anatomical definition of the organs, whilst remaining compatible with dual-mode imaging techniques.

The expression "pharmaco-organ" is understood in a known manner in the present description to mean a patch of the organism exhibiting an identical response to tracers, so that the pharmaco-organs are not totally identifiable to the organs. For example, the kidney organ may be split into at least two pharmaco-organs: the cortex of the kidney and the pelvis, in which organs the tracers exhibit kinetics on account of the time required for the filtration of the blood by the cortex of the kidney to form urine in the pelvis.

The term "tracer" is understood to mean in a known manner in the present description a molecule involved in the biological mechanisms studied and marked in such a way as to be able to be trapped in the organism. This molecule is injected intravenously at "tracer" dose, that is to say large enough to be tagged, but low enough not to disturb the operation of the organism. Such a tracer, then marked by a radioactive isotope, is in particular used in molecular imaging techniques, in particular positon emission tomography (PET), gammatomography ("Single-Photon Emission Computed Tomography", "SPECT" for short), optical imaging, MRI imaging and ultrasound imaging.

By way of example of a variable of physical, chemical or biological type characterizing said sequence, use is advantageously made of the radioactive concentration at a given instant $t_0$ to $t_n$ of at least one marked active principle injected into said organism, the whole set of voxels inside each pharmaco-organ exhibiting biochemical kinetics of distribution of said active principle which are similar.

According to other characteristics of the method of the invention:
it is granted that there exists in each starting image of said sequence a partition of the space into a finite number of said structures, which are each connected and each exhibit within them a homogeneous behavior in response to a phenomenon studied of which the evolution of said variable is representative; and the number of said structures is determined a posteriori.

According to other advantageous characteristics of step a) of modeling according to the invention:
said model furthermore comprises heterogeneous parameters dependent on the spatial coordinates of the voxels within one and the same structure, and it is granted that said homogeneous and heterogeneous parameters can be estimated on one or more volume elements included in this same structure;

it is furthermore granted that said structures together exhibit different responses to said phenomenon studied, unless they are not connected;

it is furthermore granted that the noise, which is inherent in said measurements and which is due to the mode of acquisition of said sequence of starting and segmentation images, is additive;

the following two constraints are furthermore fixed, so as to take into account local mixtures of various temporal evolutions of said signal:

(i) if the totality of the voxels which are neighbors of a voxel and which contribute to the evolution of said variable relating to this voxel is included in the same structure, then said corresponding signal is a realization of the model of this structure, and (ii) said set of homogeneous parameters for these neighbor voxels is the same as that of said model specific to this structure; and in the case of an imaging technique with injection of tracer, such as PET or "SPECT", optical imaging, MRI imaging and ultrasound imaging, said model may be a compartmental model of the type with one or more independent tracers and with several compartments, such as biological compartments (it is assumed that the tracers disperse within the compartments, and this model studies the concentration of the tracer in each compartment via rates of transfer between the compartments).

According to a preferential exemplary embodiment of the invention, the model chosen is a compartmental model with four parameters, but the present method may be extended without modification to a compartmental model with six parameters. This modeling presupposes that the organs are healthy. In the event of organs exhibiting pathological zones, the latter will be dealt with through a separate model, and will therefore be segmented separately from the healthy part of the organ. The pathological zones of the organs may therefore be brought into relief by the present method.

It will be noted that the signal modeling implemented in this step a) involves a study of the essential mechanisms of the phenomenon at play, for example by introducing physiological parameters such as the concentration of tracer in the plasma or the tissue, or else the fraction of blood volume, in the case of pharmaco-imaging (the term "phenomenon" is understood to mean a hidden process whose effects are indirectly measurable, e.g. the "neuron activation" phenomenon which is correlated with its consumption of glucose in the case of PET imaging).

Said model used in step a) is in particular designed to make it possible to calculate analytical expressions for the measurements expected, conforming to the phenomenon studied. Comparison of these analytical expressions with the measurements of the effects of the phenomenon make it possible to estimate the parameters thereof (e.g. for the "neuron activation" phenomenon, the consumption of glucose can be measured indirectly and partially via the PET technique, by injection followed by acquisition of fluro deoxy glucose molecules marked by a positon emitter isotope).

It will be noted that these local mixtures of various temporal evolutions of the signal convey a so-called "partial volume" effect, due to the low intrinsic resolution of the camera used. The signal measured at a given voxel thus contains a mixture of the physiological kinetics of the neighboring regions of interest (e.g. neighboring pharmaco-organs).

It will also be noted that the method according to the invention makes it possible to reliably determine, to within the partial volume effect, the models of evolution corresponding to each structure of interest, such as models of kinetics of a pharmaco-organ. These models are in fact estimated in the zones of the image where the kinetic model with a single organ is the most valid. It is therefore unhelpful to refine the parameters of the models of the pharmaco-organs in the course of multiple iterations: a simple aggregation of each volume element with the model which best represents its kinetic suffices.

In the present method we choose a time-non stationary Gaussian additive noise model. The noise is estimated over the whole set of samples extracted during segmentation, and it is corrected for the influence of the signal in the case of an image sequence reconstructed by an iterative method. The method according to the invention takes into account:

the spatial non stationarity of the noise within the images reconstructed by an iterative method, by correcting the data from the influence of the signal during each step of our algorithm, and the temporal non stationarity of the noise, thereby making it possible to give different weightings to the various images of the sequence, accounting for the real variability of the data around the model.

According to other characteristics of step b) of extracting model-voxels according to the invention:

this step b) comprises a prior selection, in a space with n dimensions corresponding to said starting image sequence (for example n=38 for a sequence of given PET images), of model-voxels so that each of said structures of interest contains at its heart at least one model-voxel as well as the neighborhood of the latter;

this step b) comprises following said prior selection, the definition of a metric designed to define the distances in said space and said local extraction criterion; and it is granted in step b) that for any structure to be segmented, there exists a voxel whose neighborhood is included within the corresponding region of interest.

According to another characteristic of the invention, this step b) comprises:

a determination, for example iterative, for each structure of interest, of a sample of member voxels (i.e. a list of voxels) belonging to this structure, this membership being determined by a similitude of the evolution of said variable with the model relating to this structure, then an estimation, for each sample, of the homogeneous parameters of the model which correspond to the structure.

The term "distance" in the present description is understood to mean the distance between two measurements of the temporal evolution of said signal (e.g. measurements of kinetics in the case of measurements of radioactive concentrations by the PET technique, in particular). In general we use a weighted Minkowski distance, of which the Euclidian, Manhattan and maximum distances are particular cases. The weighting factor, which is chosen to compensate for any non stationarity of the signal, is in general taken equal to 1 for each measurement value (e.g. a determined instant of the kinetics of the concentrations).

The term "thresholding" of an image is understood to mean the operation which consists in selecting the voxels whose measure in the image is greater than a threshold and, by extension, the operation where the voxels whose measure in the image lies between two thresholds, a low threshold and a high threshold, are selected. A thresholding may therefore consist in selecting the voxels whose measure in the image is equal to a given value.

According to another characteristic of the invention, it will be noted that the boundary of each structure is excluded from the extraction of said samples which is implemented in the aforesaid step b) according to the invention.

According to another characteristic of the invention, step c) of merging and of classification comprises a merging of said samples corresponding to one and the same structure of interest, before or after said classification of the voxels. This merge is implemented for example by a hierarchical ascending classification. As regards the classification of the voxels which is also included in step c), it is for example implemented by a discriminatory analysis, it being understood that any method of ranking would be appropriate for this classification.

On completion of this step c) of merging and of classification, a label image is obtained indicating to which group of samples a given voxel is likened. Although one could be satisfied with this image, it is necessary, in order to verify the definition of a segmentation image, to separate each connected component for each label.

According to another characteristic of the invention, said method of segmentation furthermore comprises, following step c), a step of separating connected components which is implemented for each of said labels.

It will be noted that this step of separating the connected components makes it possible to separate non connected structures which exhibit similar evolutions of said variable, and that this separating step is necessary in order to go from a classification image to a segmentation image in regions of interest.

According to another advantageous characteristic of the invention, said method furthermore comprises an optional step of presegmentation which is implemented before or after step a) and which consists in separating said starting images into a first part containing said structures of interest and into a second part corresponding to an image background excluded from the segmentation.

It will be noted that this presegmentation step makes it possible not only to accelerate the implementation of the method according to the invention, but also to avoid the pollution of the segmentation of the zone of interest of the image by insignificant kinetics of structures.

According to another advantageous characteristic of the invention and independent of the preceding optional characteristic (i.e. not conditioned by the latter), said method furthermore comprises another optional step of optimizing the samples which is implemented following step b) and before step c) and which consists, for each sample, in searching with for example an iterative algorithm for a for example geometric, parametric or free shape which minimizes within it the signal of structures other than that where the model-voxel has been extracted.

For this step of optimizing the samples use will for example be made of a "region growth", i.e. an aggregation of the voxels neighboring the aggregates to these latter, by decreasing order of similitude with said model.

The following algorithm is for example proposed for extracting a sample $\psi_i$ minimizing within it the signal originating from structures other than i.

At the first iteration, the sample $\psi_i$ sought is equal to the whole set of kinetics contained in $V_j$.

At each iteration, the model of the structure i is estimated within the form $\psi_i$. Next, a region growth is effected on the basis of volume element j, maximizing at each new aggregation a criterion of similarity between the kinetic of the volume element considered and the estimated model of the structure i. The region growth ceases when the number of volume elements included in the region produced becomes sufficient to estimate the parameters $\{\theta_u(i)\}_{1 \leq u \leq U}$ of the model M for the structure i—for example equal to that contained in $V_j$. $\psi_i$ is then calculated as the set of kinetics of the volume elements of the region produced.

The iterative process ceases when $\psi_i$ ceases to evolve from one iteration to the next.

It will be noted that this optional step of optimizing the samples improves the quality and the robustness of the segmentation obtained of each structure detected, since it ensures that the sample is indeed included in the corresponding structure.

According to another advantageous characteristic of the invention and independent of each of the two preceding optional characteristics, said method furthermore comprises an optional step of hierarchical representation of said regions of interest obtained which is implemented following step c) and before said step of separating the non connected structures.

It will be noted that this optional step of hierarchical representation of the organs allows the user to choose the optional level of merging for a given structure. Too high a level of merging would not make it possible to detect the structure, which would be merged with another one, while too low a level of merging would split the corresponding part of the image into two zones representing the same structure. This hierarchical representation makes it possible, moreover, to choose a posteriori the number of structures within the image.

The present method proposes that all the segmentation images be preserved for each level of merge and that the choice be left to the user, e.g. for a given pharmaco-organ, of the level of merge where it is best segmented.

It will be noted that this method does not merge the volume elements, but the samples via the models of evolution (e.g. of kinetics of pharmaco-organs), the number of which is advantageously smaller by four orders of magnitude. "Navigation" between the various levels of merge is therefore possible and can be interpreted as a search for the level of merge which is such that all the models corresponding to the same pharmaco-organ are merged. Identification between aggregate and region of interest (e.g. pharmaco-organ) then becomes total.

In a general manner, it will be noted that the method according to the invention is applicable to the segmentation of all types of images or of sequences of starting images, e.g. satellite images.

In a general manner, it will be noted that the method according to the invention makes it possible to process a large mass of data.

Specifically, the calculation time remains compatible with the requirements of users, even in the case of data acquisition with a camera of PET type with high spatial resolution. The complexity of the critical steps of the algorithm—extraction of the model-voxels and segmentation—is in fact proportional to the number of individuals to be ranked. Several million individuals are thus ranked without the increase in this number of individuals requiring approximations to be made during segmentation. Moreover, the present method does not require any hypotheses regarding the prevalence of certain images of the sequence over others in terms of stability of the physiological phenomena.

It will also be noted that the method according to the invention benefits from a cost in terms of calculation time which is fixed and is in particular compatible with the processing time for data arising from the PET technique.

It will be noted moreover that the present method makes it possible to segment regions of very different sizes, making no hypothesis as to the size of the structures to be segmented, such as pharmaco-organs.

The aforesaid characteristics of the present invention, as well as others, will be better understood on reading the following description of several exemplary embodiments of the invention, given by way of non limiting illustration, said description being offered in conjunction with the appended drawings, in which:

BRIEF DESCRIPTION OF THE DRAWINGS

FIGS. 6a and 6b illustrate two analyses of presegmentation histograms illustrating the extraction of the index of the minimum of a histogram situated between the two peaks corresponding respectively to the rat organism of FIG. 4 and to the image background of FIG. 5, this index corresponding to a thresholding value making it possible to separate the volume elements of the rat organism from those of the background, FIGS. 7a and 7b are two masked images obtained by presegmentation on the basis of oligo-nucleotides injected into this rat, these two images corresponding respectively to FIGS. 6a and 6b, FIGS. 8a and 8b are two images of coronal sections of rat organisms, obtained during the step of extracting model-voxels according to the invention, image 8a illustrating a coronal section passing through the heart and the kidneys and image 8b illustrating a coronal section passing through the bladder, FIGS. 9a and 9b are two images of coronal sections which derive respectively from FIGS. 8a and 8b and which illustrate the local minima of the variances of non reconstructed data, that were obtained in the core of the organs by principal component analysis.

DESCRIPTION OF THE PREFERRED EMBODIMENTS

In the following account of the method according to the invention, the following notation is used:
- i: an organ, a label or a sample and I: the number of samples.
- o: an organ.
- t and t': instants or indices of images of the sequence.
- $\Delta_t$: the duration of acquisition of image t of the sequence.
- j and k: volume elements (voxels).
- s: an injected tracer and S the number of injected tracers.
- r: a radius.
- $C_j$: variation of the concentration within volume element j over time, which hereinafter will be dubbed the kinetic.
- $V_j$: the neighborhood of the volume element j.
- $\psi_j$: a sample of kinetics representative of the model of structure i.
- Cp(t): the plasmatic kinetic, constant in the organism.
- Ca(t): the arterial kinetic, constant in the organism.
- $Cf_i(t)$: the kinetic of the free compartment.
- $Cb_i(t)$: the kinetic of the bound compartment.
- $Ct_i(t)$: the kinetic within the tissue: $Ct_i(t)=Cf_i(t)+Cb_i(t)$.
- $M_{i,j}(t)$: the kinetic predicted by a single-organ model, organ i within volume element j.
- $\epsilon_j(t)$: the detection and reconstruction noise at volume element j.
- $\sigma$: the standard deviation of the noise
- $K_1$, $k_2$, $k_3$ et $k_4$: the parameters of a model with three compartments.
- $Vb_{i,j}$: the plasmatic volume ratio within volume element j of organ i.
- $\mu_i(t)$: the mean kinetic of model $M_{i,j}(t)$ within organ i.
- $\beta_{j,k}$: the coefficient of contamination of the kinetic of volume element j by that of volume element k, and vice versa.
- i(k): the notation signifying that i depends on k. Here we have organ i physiologically present in volume element k.
- $n_j$: the number of zero or negative values of the kinetic $C_j(t)$ at volume element j.
- $Mode_{found}$: the peak of the histogram corresponding to the background.
- $Mode_{org}$: the peak of the histogram corresponding to the organism.
- nmin: m'index of the minimum of the histogram situated between $Mode_{org}$ and $Mode_{fond}$ corresponding to a threshold value making it possible to separate the volume elements of the imaged organism from those of the background.
- $B_{j,r}$: the ball of radius r centered at j.
- $\mu_j(t)$: the mean of the kinetics $C_k$ within the ball $B_{j,r}$.
- $e_{j,l}(t)$: the $l^{th}$ eigenvector and $\lambda_{j,l}$: the $l^{th}$ eigenvalue of the principal component analysis calculated on the kinetics of the volume elements included in the ball $B_{j,r}$.

Figure 1:
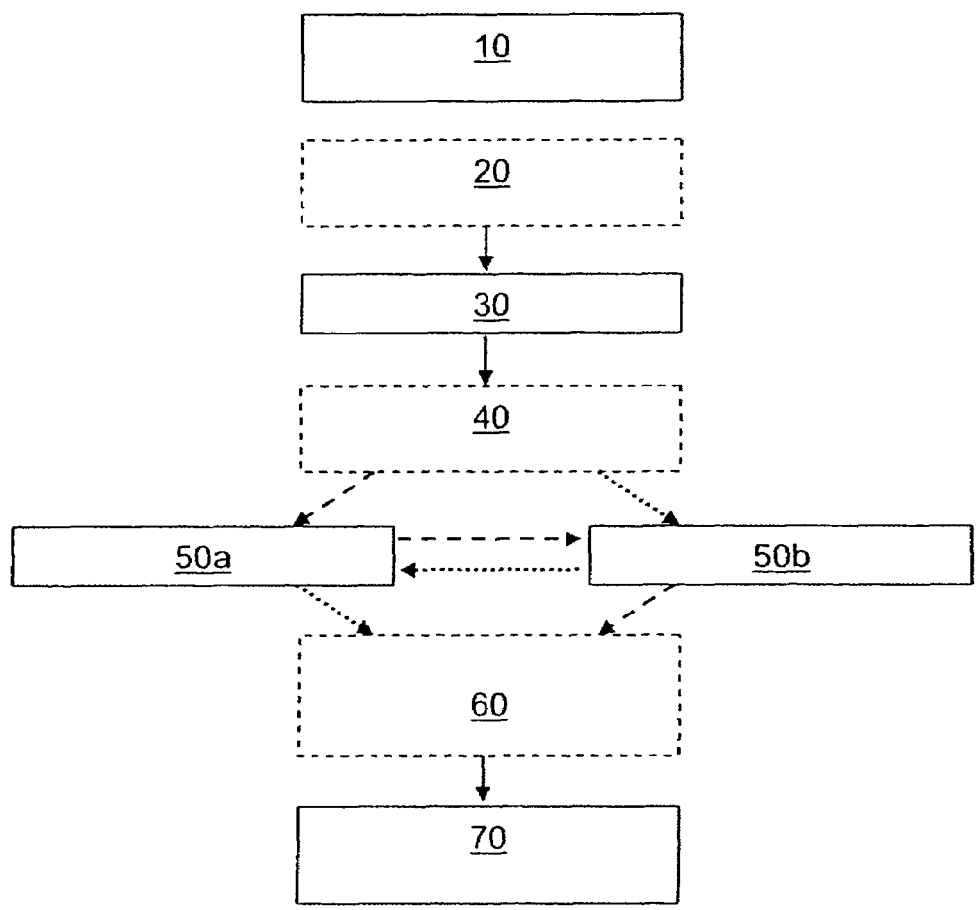
FIG. 1 is a block diagram illustrating the various compulsory or optional steps of the method of segmentation according to the invention.
Figure 2:
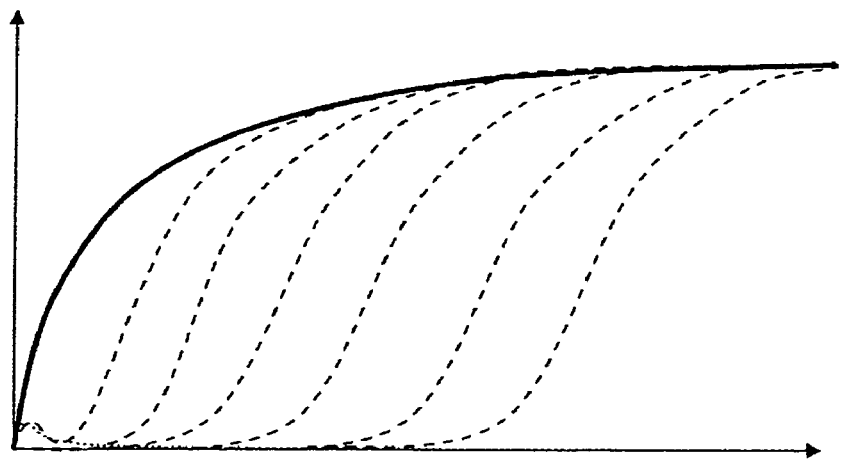
FIG. 2 is a chart illustrating in particular the families of non physiological kinetics which are generated by the deployment of bladders of rats, in an image acquired by the PET technique.

The method according to the invention, the main obligatory and optional steps of which are illustrated in FIG. 1, is preferentially implemented via the PET imaging technique. It will be noted however that this method of the invention is in no way limited to this technique.

The diagram of FIG. 1 illustrates the eight steps of this method, five of these steps 10, 30, 50a, 50b and 70 being obligatory (symbolized by solid boxes) and three other steps 20, 40 and 60 being optional (symbolized by dotted boxes).

A first step 10, essential in the method according to the invention, consists of a modeling of the signal within the image, via the definition of a model tailored to the phenomenon studied. This model is defined once and for all for a given phenomenon, and therefore need not be redefined for a new image pertaining to this phenomenon. The data of this model will subsequently make it possible not only to determine whether a given volume contains the kinetics originating from a single structure, but also to define a distance between a kinetic and a sample of kinetics that is assumed to be representative of a given structure.

If necessary, a second optional step 20 of presegmentation of the image will separate the latter into two parts, one of these parts corresponding to the zone studied, such as an organism with the PET technique, and the other part corresponding to the image background, judged to be of no interest.

A third step 30, likewise essential in the method according to the invention, consists of an extraction of model-voxels at the core of each structure of interest, made possible by the measure of the presence of a single model of kinetic of structure within the neighborhood of each voxel of the image. One and the same structure can then contain several model-voxels.

It is possible to preserve the neighborhoods defined hereinabove of the model-voxels extracted as samples of points situated in the organs. However, for a given model-voxel, it may be judicious to implement a fourth optional step 40 of optimizing the samples, in which the search for a sample whose shape is most tailored to that of the structure within which the model-voxel was extracted. This new sample can for example be extracted by a known method of region growth.

Two steps 50a and 50b, both compulsory, are then implemented according to one or the other of the two embodiments according to the invention described below.

According to a first embodiment, step 50a of ranking the kinetics is implemented following step 30 or 40, in which each volume element of the image is aggregated with the sample whose model is closest to that of this element. Next we implement step 50b of merging the samples, where the samples belonging to one and the same organ are merged.

According to a second embodiment, step 50b of merging the samples is implemented following step 30 or 40, then we implement step 50a of ranking the kinetics.

If the merging step 50b uses a hierarchical method, this merging hierarchy can be used to describe the structures in an optional step 60 of hierarchical representation of the organs, a given structure appearing on a span of given levels of merge. In an ideal particular case, the intersection of all the spans of appearance of the structures is non empty and can be extracted automatically. In a converse case, the choice can be left to the user, for each of the structures, of the span of merging levels for which it appears to be the best.

At this step 60 is obtained an image of aggregation of the volume elements with the merges of samples of which they are most similar.

However, since two structures may exhibit identical responses to the phenomenon studied while being disjoint, we preferentially implement an optional step 70 of separating the connected components, which makes it possible to separate such structures.

On completion of the implementation of this method of the invention, a segmentation of the image in accordance with the chosen signal model is available.

More precisely, the method of segmentation according to the invention may be broken down as follows.

We study a phenomenon whose effects are measurable at each point of the discretized space—image—and whose measurement comprises T values (T>1)—these values may for example be the measurements of the phenomenon at successive moments. In what follows, the ordered series of the T values of the measurement will be called the "kinetic".

Let us call S the noiseless measurement of this phenomenon at each point of space. Let us call C the real measurement, subject to the limitations of the detection model used.

The main hypotheses and constraints on which this method according to the invention is based will be detailed hereinafter:

Hypothesis H1: there exists a partition of space into a finite number of structures each exhibiting homogeneous behavior within it and such that each of these structures is connected.

The present method therefore seeks to produce such a partition within the image, based on the information contained in the real measurements C. To do this, we shall begin by defining a signal model based on the modeling of the phenomenon itself. This model will enable us to perform a measurement of the presence of several structures in a small volume. This measurement is necessary for the step of extracting the model-voxels. Moreover, the probability that a volume element belongs to a structure will be determined by the similarity of the kinetic of this volume element with the model of the structure.

Signal Modeling Step 10:

Let us define a parametric model $M(\theta_u(i), \phi_v(j))$ of the phenomenon, certain of whose parameters $\{\theta_u(i)\}_{1 \leq u \leq U}$ depend only on the structure studied i and are consequently homogeneous within this structure. The other parameters $\{\phi_v(j)\}_{1 \leq v \leq V}$ of the model M depend on the position j in space. The parameters $\{\phi_v(j)\}_{1 \leq v \leq V}$ v are therefore variable within one and the same structure. We shall subsequently denote by $M_{i,j}$ the realization of the model of kinetic for structure i at volume element j. The smaller the number V of parameters $\phi_v(j)$ the more constrained is the model. We shall choose M such that at any point j of i, we can assume $S_j = M_{i,j}$.

The response of a structure to the phenomenon studied is characterized by the set of parameters $\{\theta_u(i)\}_{1 \leq u \leq U}$ whose value is specific to structure i and homogeneous within the latter. M will therefore be chosen in such a way that two structures with different behaviors each exhibit a different parameter set $\{\theta_u(i)\}_{1 \leq u \leq U}$.

Hypothesis H2: the parameters of $M_{i,j}$ may be estimated over a measurement sample included in i and of sufficiently large size.

Hypothesis H3: the structures whose contours we seek to delimit exhibit between them different responses to the phenomenon studied, unless they are not connected.

Two connected structures exhibiting the same response to the phenomenon will therefore be considered to be one single structure.

Hypothesis H4: The measurement noise due to the mode of acquisition and reconstruction of the image is additive.

From this we conclude that the measurement $C_j$ within the volume element j may be expressed as:

$C_j = S_j + \epsilon_j$ where the noise $\epsilon_j$ may be non stationary both from a spatial and temporal point of view.

Consequently, if j is included in i, $C_j$ may be written:

$$C_j(t) = M_{i,j}(t) + \epsilon_j(t).$$

Once the parameters $\{\theta_u(i)\}_{1 \leq u \leq U}$ of the model of structure i have been estimated, it becomes possible to calculate the reconstruction error $\epsilon_j(t) = C_j(t) - M_{i,j}(t)$ for any volume element j of the image.

This reconstruction error is an indicator of the presence of structure i at voxel j.

The problem of local mixtures of kinetics will be examined now.

In the case where $S_j$ is not equal to $M_{i,j}$, but to a known function $f_j$ of the realizations $M_{i(v_k),v_k}$ of the models of the structures $i(v_k)$ present at the volume elements $v_k$, the $\{v_k\}_{1 \leq k \leq K}$ being the neighbors of j. The signal within a given volume element j may be written $S_j = f_j(\{M_{i(v_k),v_k}\}_{1 \leq k \leq K})$.

However, if all the neighbors $\{v_k\}_{1 \leq k \leq K}$ are included in i, $S_j = f_j(\{M_{i,v_k}\}_{1 \leq k \leq K}) = N_{i,j}$.

Constraint C1: M must satisfy two conditions:

(i) if all the neighbors $\{v_k\}_{1 \leq k \leq K}$ are included in i, then N must always be a realization of the parametric model M; and (ii) the parameter set $\{\theta_u(i)\}_{1 \leq u \leq U}$ of N must be the same as that of M.

In the case where all the neighbors $\{v_k\}_{1 \leq k \leq K}$ are included in i, we can then define a function h of j such that:

$$S_j = M_{i,h(j)} \text{ and } C_j(t) = M_{i,h(j)}(t) + \epsilon_j(t).$$

In the case of a linear function $f_j$, $M_i$ must depend linearly on j.

In the case where $f_j$ is a barycenter with positive coefficients, $M_i$ must be a convex function of j.

Presegmentation Step 20:

In certain cases, the image to be segmented contains a large number of volume elements whose n dimensional measurement corresponds to an absence of signal. These volume elements may then be grouped together into one and the same region. The kinetic model is meaningless in such regions, and the estimated models will not correspond to any phenomenon, bar noise. Any analysis conducted in such regions is a loss of time, which may be considerable when their size becomes non negligible with respect to the total size of the image.

On account of the random nature of the measurement C within such regions, we can expect to extract therefrom a large number of model-voxels during the extraction step 30. The models extracted being themselves random, they will be very different from one another and the probability of them all being merged in one and the same region is small. The application of the algorithm to the zones of the image exhibiting no signal will slow it down and will disturb the extraction step 30 and the step 50b of merging the samples.

It is therefore advantageous to isolate, during this step 20, the zones exhibiting no signal, which we shall dub "exterior", from the zones exhibiting a signal, which we shall dub "interior".

It will be noted that many operations make it possible to perform such a separation, such as for example a thresholding.

Model-Voxels Extraction Step 30:

Let $H0_{V_j}$ be the hypothesis according to which the neighborhood $V$ of the volume element j contains only kinetics originating from the model of a single structure.

This crucial step of the method according to the invention will extract points whose neighborhood maximizes a criterion of inclusion in a structure. Step 10 of modeling the signal present in the image makes it possible to define this criterion as the measure of the validity of the hypothesis $H0_{V_j}$. If a model with a single structure is incapable of sensing the signal within the neighborhood considered, then it is probable that the latter contains the kinetic models of several structures.

However, this step requires a further hypothesis, which ensures that points interior to each structure are extracted:

Hypothesis H5: For any structure, there exists a volume element j whose neighborhood $V_j$ lies within the organ.

According to this hypothesis, any structure i to be segmented contains an identical shape to that of V known and determined a priori. Non compliance with this condition would give rise to an uncertainty as to the detection of this structure.

In the case where the signal present within a volume element j is calculated as a function $f_j$ of the models of the structures at the neighboring volume elements, hypothesis H5 becomes:

Hypothesis H5': For any structure, there exists a volume element whose neighborhood lies within the organ, and of which and such that for any k belonging to this neighborhood, the domain of application of $f_k$ is likewise included in the structure.

Indicator of the Interior of the Organs:

Consider a measure $\Gamma_{V_j}$ of the validity of hypothesis $H0_{V_j}$ within the neighborhood $V_j$ of j comparable between two points of space. Any non stationarity of the noise—either spatial or temporal—will therefore have to be taken into account in the calculation of this measure. This measure $\Gamma_{V_j}$ is calculated for each volume element of the image—or of the zone of interest extracted during step 20.

Extraction:

Large values $\Gamma_{V_j}$ correspond to volume elements j each point of whose neighborhood $V_j$—according to hypothesis H5—or whose domain of application of $f_k$ for any k belonging to $V_j$—according to hypothesis H5'—is included in the same structure. Specifically, hypothesis $H0_{V_j}$ becomes invalid within the $B_{j,r}$ when $B_{j,r}$ straddles two structures i and o characterized by different responses to the phenomenon studied.

We therefore extract the local maxima of $\Gamma_{V_j}$, the measure of validity of $H0_{V_j}$ calculated for each volume element j of the zone of interest of the image (a local maximum j of a measure $\Gamma$ is such that, for any k neighboring j, we have $\Gamma_{V_j} \geq \Gamma_{V_k}$).

This step 30 of the method according to the invention will detect points in the neighborhood of which only one model of a structure is produced. In the case of a local mixture of kinetic through a function $f$, the points for which hypothesis H5' is not satisfied, although the neighborhood $V_j$ is included in the organ, are not therefore certain to be detected.

A fortiori, this is true for structures whose size is of the order of the resolution of the image (and not of the acquisition device), and also for fine and elongate structures exhibiting no bulging. However, the extraction of local maxima of the criterion makes it possible to extract points within regions of size or of thickness that is less—but not negligible—than the size of the neighborhood considered. It will however be noted that the estimation of the model in such regions will be polluted by the models of kinetics of the neighboring structures.

Samples Optimization Step 40:

For a given geometry of neighborhood $V_j$ and in accordance with the model M of the phenomenon studied, the kinetics contained in $V_j$ constitute a locally optimal sample of kinetics of the structure i containing j. The kinetics at the volume elements contained in $V_j$ may therefore be chosen as samples of kinetic of structure i.

However, certain structures may have a very different geometry from that of V and may not have sufficient bulges for there to exist a neighborhood $V_j$ satisfying H5 or H5'. The neighborhood $V_j$ surrounding a voxel j extracted during step 30 may therefore serve as initialization for an iterative algorithm searching for a shape which minimizes within it the signal of structures other than i. This shape may be geometric (ellipse, cylinder), parametric (beta-splines) or else of free form.

According to the present invention, an algorithm making it possible to extract a sample $\psi_i$ minimizing within it the signal originating from structures other than i may be as follows.

At the first iteration, the sample $\psi_i$ sought is equal to the whole set of kinetics contained in $V_j$.

At each iteration, the model of structure i is estimated within the form $\psi_i$. Next, a region growth is effected on the basis of volume element j, while maximizing with each new aggregation a criterion of similarity between the kinetic of the volume element considered and the estimated model of structure i. The region growth ceases when the number of volume elements included in the region produced becomes sufficient to estimate the parameters $\{\theta_u(i)\}_{1 \leq u \leq U}$ of the model M for the structure i—for example equal to that contained in $V_j$.

$\psi_i$ is then calculated as the set of kinetics of the volume elements of the region produced.

The iterative process ceases when $\psi_i$ ceases to evolve from one iteration to the next.

We have thus determined a new sample $\psi_i$ of kinetics of structure i, the form of which locally optimizes the estimate of the model M of the phenomenon studied for structure i.

Kinetics Classing Step 50a:

The definition of the samples gives direct access to the models of kinetics of structures i which make up the image. The classification of the kinetics—a generally iterative process in the course of which the parameters of the model are estimated—reduces here to a straightforward classing: each volume element of the image is aggregated with the structure whose model accounts best for its kinetic.

In the event of noise which is non stationary from a spatial point of view, the noise may be "whitened", unless the variance of the noise is estimated within the samples. It may also be calculated analytically if the spatial dependence of the variance of the noise follows a law known a priori.

Let us note that the noise may be estimated within the samples by the relation:

$$\sigma_i^2(t) = \sum_{k \in \psi_i} (C_k(t) - M_{i,k}(t))^2.$$

Samples Merging Step 50b:

The extraction step 30 can extract several model-voxels within one and the same structure. Also, the resulting aggregation image is hardly utilizable as such, since a volume element belonging to a structure is assigned randomly to one of the samples associated with this same structure.

We have I samples, several of which may be found within the same structure. The samples included in the same structure must therefore be merged, so that each merged class obtained corresponds to a structure. A measure of similarity between the models $M_i$ and $M_{i'}$ estimated over the samples i and i' should be determined. Two samples i and o contained in the same structure will be characterized by similar values of parameters $\{\theta_u(i)\}_{1 \leq u \leq U}$ and $\{\theta_u(i')\}_{1 \leq u \leq U}$, since the latter are specific to the structure that they represent. The similarity between the samples i and i' may be determined either directly on the basis of the parameters $\{\theta_u\}_{1 \leq u \leq U}$ defining the model, or in the guise of error of reconstruction of sample i (respectively i') by the model of sample i' (respectively i), or by primitives extracted from the kinetics reconstructed by the models (maximum, moment of realization of the maximum, etc.), or else by a function incorporating these various elements.

The merge will amalgamate by priority the samples for which the similarity between their respective models is a maximum. A merge of samples will be considered to be a new sample, thereby making it possible to repeat the merging step.

The parameters $\{\theta_u(i)\}_{1 \leq u \leq U}$ and $\{\theta_u(o)\}_{1 \leq u \leq U}$ of the models of two structures i and o being different in terms of parameters, they will be merged after the merges of the samples representing the same structure. Hence, theoretically there exists a step of merging after which to each structure detected there corresponds exactly to a group of merged samples. This particular merging step may for example coincide with a sudden decrease in the measure of similarity between the models of the two merged samples. This optimal merging step may therefore be determined by studying the measure of similarity or else its derivatives with respect to the merging step.

Step 60 of Hierarchical Representation of the Organs:

The allocation of one and the same label to the regions merged by the merging step 50b makes it possible theoretically to obtain a classing image in which each structure corresponds exactly to one merge of samples, and to do so for a merging step which is identical for each structure studied.

However, the responses of certain structures to the phenomenon may be very similar without being identical, and this would not ensure that the samples corresponding to different structures would be merged after those which correspond to the same structure. No "level of merge" will then exist such that each structure—or each group of structures exhibiting exactly the same response to the phenomenon observed—corresponds exactly to a sample.

It is also conceivable for this optimal level of merge to exist, but for it to be impossible to determine on the basis of studying the measure of similarity between models of kinetics of samples to be merged. In order to alleviate these defects, the present method proposes that the image be represented in the form of a tree each leaf of which represents an aggregate obtained during the step 58 of classing the kinetics. Each node of the tree represents a merge or an aggregate arising from a merge, and the leaves of children represent the aggregates which make up this merge.

Through recognition of structures using an automatic algorithm or else through manual recognition, this step 60 undertakes to determine the node of the tree corresponding exactly to a given structure. The identification of each structure in the tree makes it possible to obtain a classing image such that to a structure there corresponds a merge of samples, but at a merging step dependent on the structure studied.

Step 70 of Separating the Connected Components:

According to the aforesaid hypothesis H3, it is possible for two structures to have the same response to the phenomenon studied, but to be non connected. Steps 50a of classing and 50b of merging, or even step 60 of hierarchical representation, may therefore amalgamate such regions under one and the same label.

A simple separation of the connected components, class by class, makes it possible to separate the structures which exhibit the same response to the phenomenon but which are non connected, and makes it possible to obtain a segmentation image, the final result of the method according to the invention.

Exemplary Implementation of the Method According to the Invention for the Segmentation of Images Arising from Positon Emission Tomography (PET)

Although the whole-body problem area for a small animal, such as a rat, is dealt with in this exemplary embodiment, the latter could equally well be applied to images of specific zones, such as the brain, and in other animals or in man. Indeed, the segmentation of the whole body is especially problematic on account of the significant physiological motions affecting the image to be processed. We have chosen a segmentation of whole-body type in a small animal to show the proper operation of the method despite the small size of the organs to be segmented and despite the occurrence of physiological motions.

It will be shown here that the kinetic model chosen satisfies the working hypotheses of the general principle, and the method followed will be described as a direct application of the general principle stated hereinabove.

a) Step 10 of Modeling the Signal:

PET Signal:

Positon emission tomography makes it possible to track what happens to one or more molecule(s) exhibiting biological properties of interest, that has been marked previously by a positon emitting radioactive isotope. This tracer is injected intravenously into the imaged subject placed in the field of view of the camera. During the disintegration of the isotope, a positon is emitted which, after losing its kinetic energy through successive impacts with electrons, annihilates with an electron to give two photons going off in diametrically opposite directions. A detection system composed of detector rings makes it possible to detect the photons emitted and to recreate the line over which the disintegration occurred. On the basis of these events, an algorithm reconstructs an image accounting, at each location in discretized space, for the number of disintegrations that took place in this volume element.

A pharmaco-organ may be defined as a structure of the organism all of whose elements exhibit an identical response to the tracer. Nevertheless, this does not signify that the kinetics measured within all the volume elements of one and the same organ is necessarily identical. It is possible to define a model of kinetic $M_{i,j}$ making it possible to account for the physiological kinetic of each of the volume elements of the pharmaco-organ. The expression physiological kinetic is understood to mean the signal emitted by the marked molecules and not the signal measured. Thus, if we assume that the noise is additive and if we ignore the partial volume effect, we can write the kinetic $C_j$, for a volume element j within an organ i as:

$$C_j = M_{i,j} + \epsilon_j$$

If we take into account the partial volume effect, which mixes with voxel j the physiological kinetics of the pharmaco-organs i(k) within the voxels k neighboring j, $C_j$ may be written:

$$C_j = \sum_{k \in Neigh(j)} (\beta_{j,k} \times M_{i(k),k}) + \varepsilon_j, \text{ where}$$

$\beta_{j,k}$ is a mixing coefficient determined by the response function of the PET imager.

The model of physiological kinetic with a single organ will have to be chosen in such a way that, for two pharmaco-organs i and o exhibiting different responses to the tracer, the number of volume elements j such that $M_{i,j}(t)=M_{o,j}(t)$ is small.

Figure 3A:
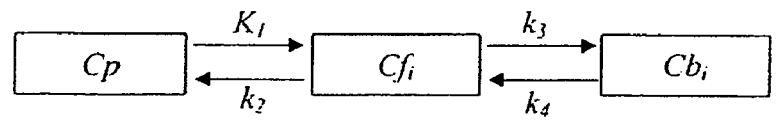
FIGS. 3a and 3b are diagrams illustrating an exemplary compartmental modeling with a single tracer of a physiological process of interaction between the tracer and an organ, via three compartments and four parameters.

Compartmental Modeling with a Single Tracer:

Let us model the physiological processes of interaction between the tracer and a given organ i by three compartments and four parameters. This tracer passes through the cellular barrier with a rate constant $K_1$. It can in the same way cross back through the barrier and return to the blood with a rate constant $k_2$. It is transformed in the cells with a rate constant $k_3$. If this transformation is reversible the inverse transformation is characterized by a rate constant $k_4$. The three compartments studied are Cp the plasma-serum compartment, $Cf_i$ the free compartment of organ i and $Cb_i$ the bound compartment of organ i. Let $Cp(t)$, $Cf_i(t)$ and $Cb_i(t)$ be the concentrations of the tracer in each of these three compartments. This process can be schematized as illustrated in FIG. 3a.

In this model, the variation of concentration of the compounds in the various components may be written:

$$\frac{dCf_i(t)}{dt} = K_1 Cp(t) - (k_2 + k_3)Cf_i(t) + k_4 Cb_i(t)$$

$$\frac{dCb_i(t)}{dt} = k_3 Cf_i(t) - k_4 Cb_i(t)$$

Initially, let us consider the case where a single tracer is injected into the organism. Let $Ct_i(t)$ be the concentration of a tracer in the tissue in organ i, $Ct_i(t)$ may be written:

$$Ct_i(t)=Cf_i(t)+Cb_i(t)$$

Figure 3B:
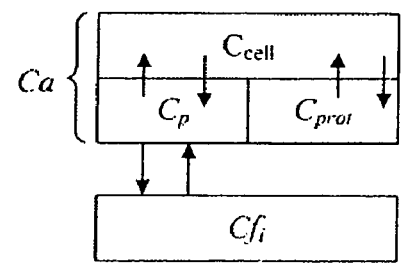

Cp(t), the concentration of the tracer in the plasmatic serum, is not directly accessible. Specifically, the compartment of the plasmatic serum is included in another compartment, the arterial compartment Ca(t). Therefore let Ca(t) be the concentration of the tracer in the arterial compartment. As illustrated in FIG. 3b, the compartment comprises a compartment $C_{cell}$ containing the cells of the blood, as well as the plasmatic compartment $C_{plasma}$, itself comprising the compartment of the plasmatic serum Cp—involved in the compartmental model chosen—and the proteins of the blood $C_{prot}$.

The kinetic model $M_{i,j}(t)$ of the PET signal within a given volume element j included in organ i may be written:

$$M_{i,j}(t)=((1-Vb_{i,j})\times Ct_i(t)+Vb_{i,j}\times Ca(t))$$

where $Vb_{i,j}$ is the arterial volume ratio within the volume element j of organ i.

Ca(t) is homogeneous in the whole organism and Ct(t) is homogeneous within a given healthy pharmaco-organ. In the case of a pharmaco-organ with pathological functioning, the latter may be separated into a healthy zone and a pathological zone. These zones behaving differently with respect to the tracer, they are pharmaco-kinetically different and will be considered to be two different pharmaco-organs.

Ca(t) and Ct(t) therefore being homogeneous within a given pharmaco-organ, $M_{i,j}(t)$ belongs to the segment Ca(t) $Ct_i(t)$, and therefore by extension to the straight line $Ca(t)Ct_i(t)$, when j varies while remaining within organ i.

We can therefore model the physiological kinetic within an organ by a straight line $D_i$ in the space of kinetics passing through Ca(t) and $Ct_i(t)$. Knowledge of the models $M_{i,j}(t)$ of physiological kinetics for a few organs i should therefore make it possible to calculate Ca(t), as the intersection of all the straight lines $D_i$. On the other hand, $Ct_i(t)$ cannot be calculated explicitly.

Compartmental Modeling with Several Tracers:

We can also show (see annex A attached), that when several tracers s—S in number—are injected into the organism, the resulting signal $S_{i,s,j}(t)$ in the volume element j still describes a straight line in the space of kinetics, this time the line passing through $$\sum_{s=1}^{S} Ct_{i,s}(t) \text{ and } \sum_{s=1}^{S} Ca_s(t),$$

on condition that these various tracers do not interact with one another.

The kinetic model therefore remains valid within the framework of the compartmental model with four parameters, whatever the number of "independent" tracers injected.

Local Mixtures of Kinetics:

Impact of the Partial Volume Effect on the Signal:

The partial volume effect can be modeled [Frouin, 2002] as a smoothing of the image. The signal $S_j$ measured in the image within a volume element j is therefore a linear combination of the kinetics $S_k$ of the neighboring volume elements k. When several tracers are injected:

$$S_j(t) = \sum_{s=1}^{S} \left[ \sum_{k \in Neighbourhood(j)} (\beta_{j,k} \times M_{i(k),s,k}(t)) \right]$$

where $\beta_{j,k}$ satisfies $$\sum_{k \in Neighbourhood(j)} \beta_{j,k} = 1.$$

$S_j(t)$ still belongs to a straight line in the space of kinetics, passing through $$\sum_{s=1}^{S} Ct_{i,s}(t) \text{ and } \sum_{s=1}^{S} Ca_s(t)$$

(see Annex A) when the neighborhood $V_j$ of j whose physiological kinetics contribute to the signal $S_j$ is included in organ i. When this neighborhood contains several organs modeled by different straight lines, $S_j(t)$ belongs to a subspace of the space of kinetics centered at Ca(t) and of dimension strictly greater than 1.

Impact of Physiological Motions on the Signal:

Non periodic physiological motions or those whose period cannot be neglected with respect to the duration of acquisition of an image of the series generate non interpretable kinetics. Specifically, at each instant t, j does not contain the same physiological sites.

The kinetics of the regions undergoing a periodic physiological motion of negligible period compared with the duration of acquisition of an image of the series, such as respiration or heart beats, become interpretable again (see Annex A).

Conclusion:

We have a model of kinetic with a single pharmaco-organ.

Consider a volume A fixed in the reference frame of the camera. Consider a volume B fixed in the reference frame of an organ, located within the pharmaco-organ i, so that the neighborhood of B (Neigh (B)) over which the partial volume effect extends is itself also included in pharmaco-organ i. Let us assume that A and B are superimposed at time $t_0$: At $t_0$ A contains only signal arising from organ i.

Let Neigh(A) be the neighborhood of A over which the partial volume effect extends. During a periodic physiological motion of small period, B moves with respect to A, so that the two volumes are no longer superimposed. However, the model $M_{i,j}(t)$ with a single organ i is valid within A, fixed in the frame of reference of the camera, if and only if Neigh(A) remains included in the organ i during the period of the physiological motion (see Annex A).

Verification of the Hypotheses of the General Principle:

Partition of the Space into Pharmaco-Organs:

The organism can be separated into a finite number of pharmaco-organs, each corresponding to an organ, to a group of connected organs or to a sub-part of an organ. By definition of the compartmental model, each pharmaco-organ is characterized by an arterial kinetic and a tissular kinetic both homogeneous in the pharmaco-organ. The aforesaid hypothesis H1 is therefore satisfied.

Estimation of the Parameters of the Model:

The model $M_{i,j}$ is a straight line in the space of kinetics. It may be estimated by means of a principal component analysis operated on the kinetics of the volume elements of the sample and centered on the mean of the signal within the sample. The aforesaid hypothesis H2 is therefore satisfied.

Different Responses of the Pharmaco-Organs to the Tracer:

A pharmaco-organ is defined by tissular and arterial kinetics that are homogeneous within it. On the other hand, there is nothing to prevent two neighboring pharmaco-organs i and o from showing an identical response to the tracer, or else $Ct_o$ from belonging to the straight line $CaCt_i$. Hence, there is nothing to ensure that the aforesaid hypothesis H3 is satisfied.

However, let us consider as a single unique pharmaco-organ two neighboring pharmaco-organs exhibiting identical responses. Hypothesis H3 is then satisfied. Nevertheless the method will be incapable of separating the two parts of this pharmaco-organ.

Measurement and Reconstruction Noise:

In PET, for iterative or analytical methods of reconstruction, the noise may be considered to be Gaussian additive, in conformity with the aforesaid hypothesis H4.

Local Mixture of Kinetics:

As we have just seen, the partial volume effect and the physiological motions generate within a given volume element a local mixture of kinetics of neighboring pharmaco-organs. In the case of the partial volume effect, we have just seen that the kinetic mixture, operated within a given volume element j, is a barycenter of the models of physiological kinetics at the neighboring volume elements. Likewise, the periodic physiological motions of small period operate within voxel j a barycenter of the models of kinetics of the pharmaco-organs which have passed through j in the course of the motion. Let us consider the case where all the neighbors of j belong to pharmaco-organ i. $M_i$ being a straight line $D_i$ in the space of kinetics, any barycenter of kinetics belonging to the straight line $D_i$ belongs to the straight line $D_i$. The aforesaid constraint C1 is therefore satisfied.

b) Presegmentation Step 20:

As indicated hereinabove in the general account of the method according to the invention, the zones exhibiting an absence of signal hamper the speed of the algorithm and the quality of the results. These signalless zones correspond in PET to the exterior of the organism: the background.

The PET image can therefore be split into two zones, one representing the organ and the other the background. The kinetics of the background are characterized by a weak signal, engendering a large number of zero or negative values, which, being non physiological, may not represent an organic kinetic. These latter, characterized by activity which is generally significant with respect to the noise, rarely cancel out and have a larger mean than the kinetics of the background.

Histogram analysis is a fast method making it possible to determine thresholds for separating several populations of volume elements. The histogram represents the number of volume elements having a given activity, or more generally whose activity belongs to a given interval. The intervals are adjoining and often take the same width.

Usual Methods:

In PET, a histogram of the transmission image will enable the organism to be readily segmented, but will hardly dissociate the latter from the objects present in the field of view: bed, device for rodents, respirator if any, etc.

The image usually used to produce a histogram from the emission is the sequence of images itself, averaged over time or else from which a particular image has been extracted. On such a histogram, the first peak represents the background or a part of the latter.

On account of the great disparity of the values within the image, a histogram-based analysis of the values of the image, though it makes it possible to detect a peak corresponding to the background, does not ensure the determination of a threshold separating this background from the remainder of the image (see FIGS. 6a, 6b and 7a, 7b).

Figure 4:
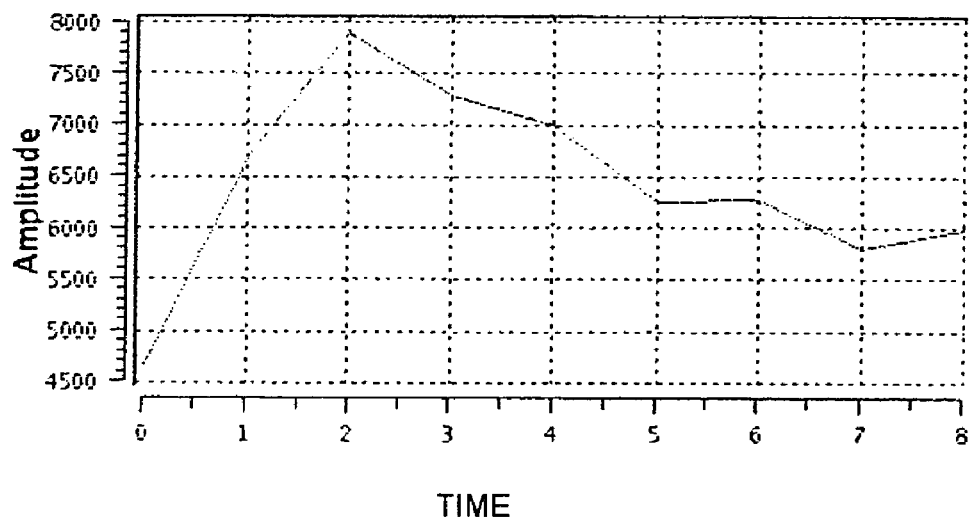
FIG. 4 is a histogram illustrating, in the case of a presegmentation according to the invention, the reduced number of negative values of a kinetic obtained by the PET technique which relates to a volume element included in a rat organism.
Figure 5:
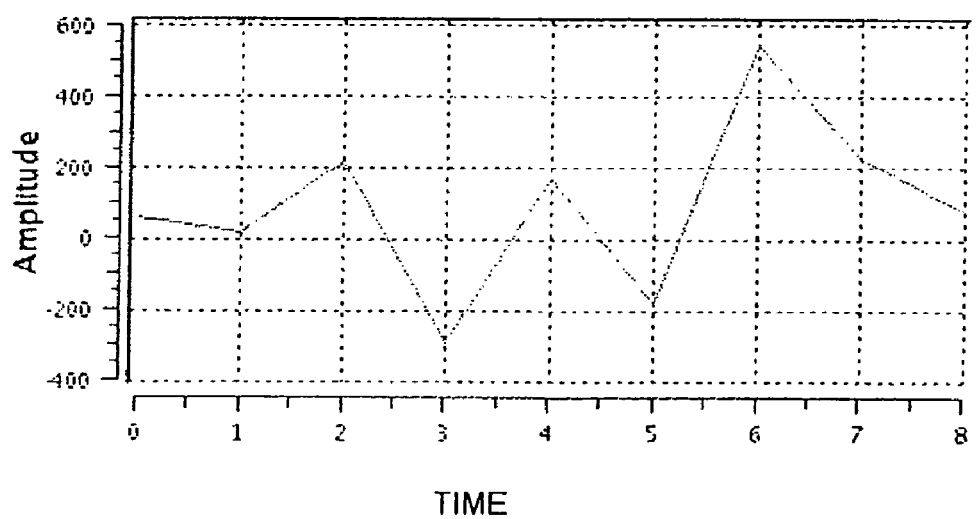
FIG. 5 is a histogram illustrating, in this optional case of presegmentation, the higher number of negative values of a kinetic relating to a volume element outside this rat organism.

Histogram of the Number of Negative Values of the Kinetics:

On the other hand, the histogram of the number of negative or zero values of the kinetic exhibits two distinct peaks—called modes—, one for the organism, which exhibits non negligible radioactivity with respect to noise, and the other for the air surrounding the organism, which exhibits negligible radioactivity with respect to noise. The kinetic of a volume element included in the organism will exhibit a small number of zero or negative values, whereas the kinetic of a volume element of the background will exhibit numerous negative values, as shown by the graphs of FIGS. 4 and 5 (respectively examples of kinetics of a volume element included in the organism and of a volume element exterior to the organism).

Let $n_j$ be the number of negative values taken by a given kinetic $C_j$. We expect $n_j$ to be large in the background and small in the organism. The histogram of the values taken by $n_j$ in the image exhibits two modes, one corresponding to the background ($Mode_{back}$) and the other to the organism ($Mode_{org}$). The latter generally exhibiting few involutions (whole body, cranium), its surface area represents a negligible number of volume elements as compared with its volume and with the volume of the background. This histogram therefore exhibits at least one minimum of index nmin situated between $Mode_{org}$ and $Mode_{back}$. A multiscale analysis of the histogram [Mangin, 1998] ensures the extraction of the minimum of index nmin of the histogram between the two modes Mode$_{org}$ and Mode$_{back}$. All the volume elements j of the image which are such that n$_j$<nmin will be considered subsequently to be in the organism, and the others to be outside the organism. A simple morphological opening on the mask obtained and an extraction of the largest connected component allow the elimination of background points attributed wrongly to the organism.

Inside the organism, certain organs, like the lungs, may exhibit very weak activity, and be excluded from the zone of interest. In order to alleviate this drawback, the zone of interest is supplemented with any background zone not connected with the edges of the image.

c) Step 30 of Extracting the Model-Voxels:

In what follows we shall take the ball B$_{j,r}$ of radius r as neighborhood V$_j$ of a volume element j. Moreover, we shall detail the embodiment only in the case of an image reconstructed by an analytic method, for which the noise within the image may be assumed to be stationary in space. The variation of this exemplary embodiment in the case of an image reconstructed by an iterative method, for which the variance of the noise is related to the signal, is given in annex C attached.

According to the model M$_{i,j}$(t) chosen previously to account for the physiological kinetic within pharmaco-organ i and for all the volume elements j included in i, M$_{i,j}$(t) belongs to a straight line in the space of kinetics. Let us consider the case of an analytic reconstruction, for which the noise is stationary in space.

Let us assume that hypothesis H5 is satisfied and that the noise within a given image of the sequence, not corrected for radioactive decay, depends essentially on the duration of acquisition of this image. Let us assume that this dependence is linear:

σ(t)=ξ/Δ$_t$, where ξ is a quantity that is stationary in time and space and Δ$_t$ is the duration of acquisition of image t of the sequence.

Let C'$_k$(t)=C$_k$(t)×Δ$_t$ be the kinetic at volume element k, whose value at time t has been weighted by the duration of acquisition of image t of the sequence. The standard deviation of the noise of the set of kinetics C'$_k$(t) thus weighted is equal to ξ. By studying the kinetics C'$_k$(t) it is possible to circumvent the temporal non stationarity of the noise.

Indicator of the Interior of the Organs:

The aforesaid hypothesis H0$_{Vj}$ is equivalent, in the present case, to a hypothesis according to which the signal within the ball B$_{j,r}$ centered at voxel j and of radius r can be modeled by a straight line in the space of kinetics, plus additive noise.

Let us no longer consider the kinetics, but the kinetics C'$_k$(t)=C$_k$(t)×Δ$_t$, it being possible moreover to assume that the noise is Gaussian. Consider a centered principal component analysis (PCA) carried out on the kinetics C'$_k$(t) within the ball B$_{j,r}$. Let $\{\lambda_{j,l}\}_{1 \leq l \leq T}$ be the eigenvalues of this PCA ranked in descending order and $\{e_{j,l}\}_{1 \leq l \leq T}$ the eigenvectors associated with these eigenvalues. Finally let μ'$_j$ be the mean of the kinetics within B$_{j,r}$ on which the PCA is centered. We shall use the variance Γ$_{Vj}$ of the data not reconstructed by the first eigenvector of the PCA relative to the signal as indicator of validity of the hypothesis H0$_{Vj}$:

$$\Gamma_{Vj} = \lambda_j^2 / \|\mu'_j\|^2, \text{ where}$$

$$\lambda_j^2 = \frac{1}{T-1} \sum_{l=2}^{T} \lambda_{j,l}^2.$$

$\lambda_j^2$ is the variance of the signal not reconstructed within B$_{j,r}$ by the PCA (see Annex B attached for the proof).

Discussion: The measure Γ$_{Vj}$ of validity of the hypothesis H0$_{Vj}$ is an approximation of the mean of the proportions of signal not reconstructed within B$_{j,r}$. This approximation has the advantage of being not very noisy, of being a good indicator of the inclusion of B$_{j,r}$ in a pharmaco-organ, but also of detecting the points whose neighborhood is, in the absence of points completely included in a given organ, at least included for the most part in the latter. Thus, pharmaco-organs exhibiting no kinetic not polluted by the physiological signals of the neighboring organs may nevertheless be detected.

FIGS. 8a and 8b illustrate maps of the IR'$_j$ in the case of an image reconstructed by an iterative method (FIG. 8a being a coronal section passing through the heart and the kidneys of the rat, in FIG. 8b a coronal section passing through the bladder of the rat).

Extraction of the Model-Voxels:

The radius r of the ball B$_{j,r}$ is chosen in such a way that the number of kinetics that it contains suffices for the calculation of the PCA. It will be taken for example equal to n×3.

We therefore calculate the map of the Γ$_{Vj}$, whose local minima correspond to points situated within the core of the organs. The neighborhood of these points is hardly affected by the partial volume effect. These local minima, which may be multiple within the same organ, are extracted automatically. In order to eliminate the local maxima due to noise, the image of the Γ$_{Vj}$ is filtered by a Gaussian filter whose variance, chosen by an iterative algorithm, is just sufficient for the number of local minima extracted to be less than a threshold fixed a priori. This threshold will be fixed relatively high so as to avoid too great a smoothing from displacing or expunging local minima corresponding to the inclusion of the ball B$_{j,r}$ in the organ.

FIGS. 9a and 9b illustrate the local minima of the map of the Γ$_{Vj}$, by extraction of the model-voxels (FIG. 9a being a coronal section passing through the heart and the kidneys of the rat, and FIG. 9b a coronal section passing through the bladder of the rat).

d) Step 40 of Optimizing the Samples:

The geometry chosen in the form of a ball B$_{j,r}$ may not be appropriate for certain pharmaco-organs of elongate, flat shapes or of "onion skin" shape. We shall therefore define a sample of connected points at j minimizing a criterion of non reconstruction by the model at an organ calculated over the kinetics of the volume elements included in B$_{j,r}$ (two connected points are such that they belong to the same region and that there exists a path included in this region that joins them).

The corrected kinetic C'$_k$(t)=C$_k$(t)×Δ$_t$ at volume element k may be written:

C'$_k$(t)=(S$_k$(t)+ε$_k$(t))×Δ$_t$.

Here we shall use the method based on region growth proposed in the general principle in order to optimize the shape of the samples ψ$_i$. This region growth, whose initial sample is formed of the kinetics of the volume elements included in B$_{j,r}$, will use the inverse of the proportion of signal of C'$_k$(t) not reconstructed by the eigenvector associated with the largest eigenvalue of the centered PCA calculated on ψ$_i$ as measure of similarity between a kinetic C'$_k$(t) and the sample ψ$_i$. Let p'$_{j,k}$ be this non reconstructed proportion of signal:

$$p'_{j,k}(t) = \frac{\sum_{t=1}^{T}\left(\varepsilon_{j,k}(t) \times \frac{\Delta_t}{\max_{1 \le t' \le T}(\Delta_{t'})}\right)^2}{\|C'_k(t)\|^2} = \frac{\|\varepsilon'_{j,k}(t)\|^2}{\|C'_k(t)\|^2}$$

is of the order of $$\frac{\xi^2}{\|C'_k(t)\|^2}$$

<<1 within the organ, and of the order of 1 outside the organ, where $\varepsilon_{j,k}(t)$ still contains non reconstructed signal. It is also large at the boundary of the organism, since $\|C'_k(t)\|^2$ decays strongly there whereas $\varepsilon_{j,k}(t)$ remains of the order of $\xi$ there. It therefore makes it possible not only to discard the kinetics that are too far from the model, but also to avoid, in the case of an organ i exhibiting strong activity polluted by the activities of neighboring organs, to prefer a weak kinetic to a kinetic of organ i.

At each step of refinement of the sample, a PCA is therefore calculated over $\psi_i$, then a region growth by front propagation is operated on the basis of volume element j, sole constituent of the region at the start. At each step, the volume element k of the front which minimizes $p'_{j,k}(t)$ is aggregated with sample i. The introduction of an Ising model makes it possible to regularize the contours of the samples obtained. The final size of each sample is taken equal to the number of volume elements included in the ball $B_{i,r}$.

Figures 10A, 10B:
FIGS. 10a and 10b are two images of coronal sections which derive respectively from FIGS. 9a and 9b and which were obtained following the step of extraction by a step of optimizing the samples according to the invention implemented by region growth.

FIGS. 10a and 10b illustrate the result of the region growth on the samples (FIG. 10a being a coronal section passing through the heart and the kidneys of the rat, and FIG. 10b a coronal section passing through the bladder of the rat).

e) Step 50a of Ranking the Kinetics:

The noise of the kinetics $C_k$ is considered to be stationary in space, and the noise of the kinetics $C'_k$ is considered to be stationary in space and time. The a posteriori probability of data item $C'_k$ knowing the model $M'_{i,k}$ may be written:

$$p(C'_k / M'_{i,k}) = \gamma \times e^{-\frac{\|C'_k - M'_{i,k}\|^2}{2 \times T \times \xi^2}},$$

where $\gamma$ is a scalar independent of organ i like the volume element k considered.

Once the models $M'_{i,k}$ have been calculated on the basis of the kinetics $C'_k$ within each sample by a principal component analysis of which only the eigenvector associated with the largest eigenvalue will be retained, the maximization of $p(C'_k / M'_{i,k})$ amounts to finding the sample i which minimizes $\|C'_k - M'_{i,k}\|^2$.

The label o such that:

$$o = \arg \min_i \|C'_k - M'_{i,k}\|^2$$

is therefore allocated to volume element k.

Regularization of the Ranking of the Kinetics:

In order to limit the chances of an erroneous aggregation of k on account of noise, we define the process of segmentation of volume element k no longer as:

$$o = \arg \min_i \|C'_k - M'_{i,k}\|^2,$$

but as $$o = \arg \max_i \left( \sum_{j \in Neigh(k)} \left[ \beta_{j,k} \times e^{-\frac{\|C'_k - M'_{i,k}\|^2}{2 \times T \times \xi^2}} \right] \right),$$

where Neigh(k) designates the set of volume elements neighboring volume element k, and $\beta_{j,k}$ a weighting factor dependent on the distance between volume elements j and k.

Figure 11A:
FIGS. 11a and 11b are two images of coronal sections which derive respectively from FIGS. 9a and 9b and which were obtained following a step of ranking the kinetics according to the invention into one hundred classes.
Figure 11B:

FIGS. 11a and 11b illustrate the ranking of the kinetics into 100 classes (FIG. 11a being a coronal section passing through the heart and the kidneys of the rat, and FIG. 11b a coronal section passing through the bladder of the rat).

f) Step 50b of Merging the Samples:

The step of extracting the model-voxels can extract several model-voxels within a given organ. Also the resulting segmentation image is hardly utilizable as such, since a volume element belonging to a pharmaco-organ is assigned randomly to one of the samples associated with this same pharmaco-organ.

We have I samples, several of which may be found within the same organ. A hierarchical ascending classification (HL) [Jain, 1988] makes it possible to merge the samples.

Two samples have a good chance of representing the same organ if the kinetics of one are reconstructed well by the model with a single organ estimated on the other, and if the mean kinetics of each of them exhibit similar activity peaks (in terms of position and intensity).

In the case of an analytical reconstruction, the variance of the noise associated with the kinetics $C'_k(t) = C_k(t) \times \Delta_t$ is equal to $\xi^2$, stationary in space and time. Let $$\lambda_i'^2 = \frac{1}{T-1} \sum_{l=2}^{T} \lambda_{i,l}'^2$$

be the mean of the T−1 smallest eigenvalues of a PCA calculated on the kinetics $C'_k(t)$ with sample i. $\xi^2$ may be estimated as the mean of the $\lambda_i'^2$ over the samples:

$$\xi^2 = \frac{1}{I} \sum_{i=2}^{I} \lambda_i'^2.$$

The cost function for merging two samples a and b may thus be written:

$$C_{a,b} = \beta \times \max\left[\frac{1}{N} \times \sum_{k \in a} \frac{\|\varepsilon'_{b,k}\|^2}{\xi^2}, \frac{1}{N} \times \sum_{k \in b} \frac{\|\varepsilon'_{a,k}\|^2}{\xi^2}\right] +$$
$$\delta \times (1 - \min[\|\mu_a\|_\infty / \|\mu_b\|_\infty, \|\mu_b\|_\infty / \|\mu_a\|_\infty]) +$$
$$\gamma \times \left(1 - \min\left[\frac{tmax_b}{tmax_a}, \frac{tmax_a}{tmax_b}\right]\right),$$

$tmax_a$ being the instant at which $\mu_a$ is a maximum. It will be noted that the phase discrepancies of the kinetics are more strongly penalized at early times, characterized by fast kinetics, than at late times, characterized by slow kinetics. The latter criterion makes it possible to dissociate two pharmaco-organs with similar kinetics, but whose kinetics models exhibit a slight phase offset.

The weights $\beta$, $\delta$ and $\gamma$ are fixed heuristically at $\beta=0.5$, $\delta=0.25$ and $\gamma=0.5$.

Between two groups of samples $G_a$ and $G_b$ that may each contain several samples, we define the following cost function $$C_{Ga,Gb} = \max_{a \in ga, b \in gb} (C_{a,b}),$$

the calculation of which is extremely fast, once $C_{a,b}$ has been calculated for any pair (a, b).

Initialization

Initially, each sample forms a group within which it is found on its own. The cost of merging each sample pair is calculated.

Merging Step

At each step of the hierarchical ascending classification, the two groups of samples $G_a$ and $G_b$ for which the merge cost $C_{Ga,Gb}$ is a minimum or merged into a new group $G_c$.

End of the Algorithm

Figure 12:
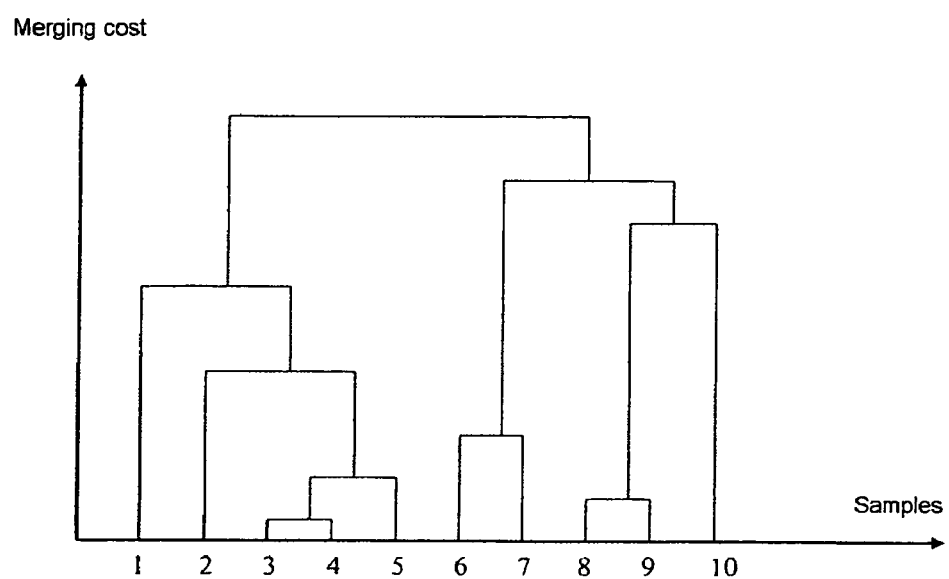
FIG. 12 illustrates an exemplary merge tree obtained by a step of merging the samples according to the invention which follows on the step of ranking of the kinetics and which is implemented by a hierarchical ascending classification.

The process ceases when all the samples have been merged. The sequence of merges between samples is retained in the form of a tree illustrated in FIG. 12.

The merge level E corresponds to an image of ranking of the kinetics between E samples. In order to obtain an associated segmentation image, it is necessary to dissociate the zones tied to the same sample, but not connected together. This operation is carried out by extracting the connected components for each label. Only the connected components exhibiting a volume greater than the smallest volume expected for a pharmaco-organ will be retained. The assigning of a different label for each of these connected components makes it possible to obtain a partition of the image into regions, that is to say a segmentation.

Figures 13A, 13B, 13C, 13D:
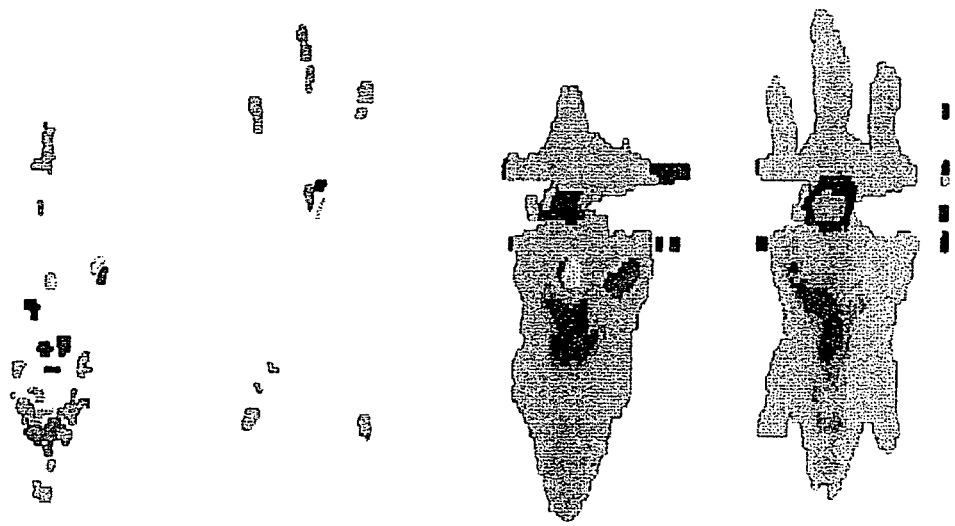
FIGS. 13a and 13b are images of coronal sections which derive respectively from FIGS. 11a and 11b and which were obtained by merging the samples via a hierarchical ascending classification, where eighteen classes have been preserved.
FIGS. 13c and 13d are images of coronal sections which derive respectively from FIGS. 13a and 13b and which were obtained by merging the labels of the image of ranking of the kinetics via a hierarchical ascending classification, where eighteen classes were preserved.

FIGS. 13a and 13b result from a merging of the samples by hierarchical ascending classification, and FIGS. 13c and 13d result from a merging of the labels of the image of ranking of the kinetics by hierarchical ascending classification, 18 classes having been retained for each of these figures (FIGS. 13a and 13c being coronal sections passing through the heart and the kidneys of the rat, and FIGS. 13b and 13d coronal sections passing through the bladder of the rat).

Figure 14A:
FIGS. 14a, 14b and 14c are "3D" segmentation images respectively obtained by this step of merging according to coronal, sagittal and oblique views.
Figure 14B:
Figure 14C:

FIGS. 14a, 14b and 14c are "3D" views of segmentation after merging, respectively coronal, sagittal and oblique.

g) Step 60 of Hierarchical Representation of the Organs:

The merge tree for the regions makes it possible to represent the segmented image not in the form of a label image, but of a tree of label images, each node or leaf of which corresponds to a group of pharmaco-organs at a step of the merge. It is therefore possible to track, by means of viewing software, the merging of the various label zones of one and the same organ. We leave the choice to the operator of the level of merge that he deems optimal for the recognition of a given pharmaco-organ. Specifically, this optimal level of merge may be different for two different pharmaco-organs.

Figure 15:
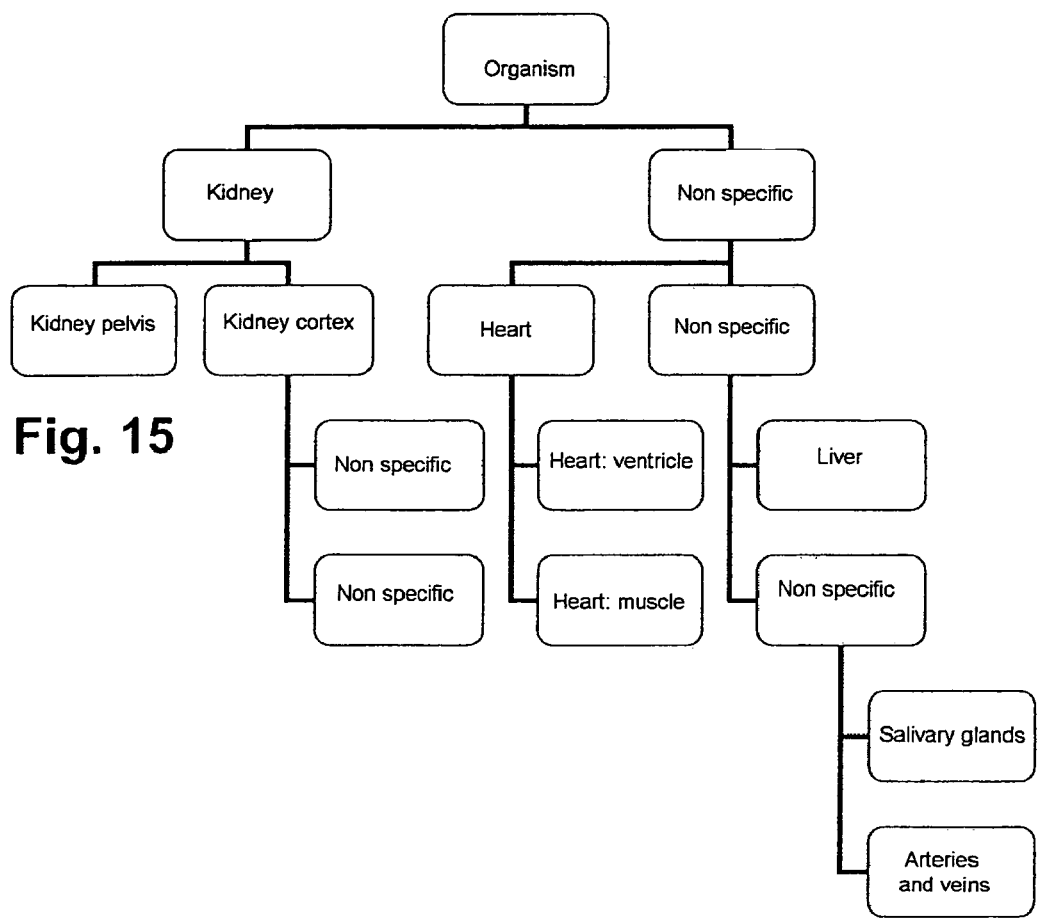
FIG. 15 is a block diagram illustrating a hierarchical representation of the pharmaco-organs according to the invention which may be implemented following this step of merging the samples.

FIG. 15 illustrates an exemplary hierarchical representation of the organs of the rats examined.

h) Step 70 of Separating the Connected Components:

The connected components of each aggregate obtained by the previous steps are separated by a method of merging labels. To each volume element is allocated an index number. The index numbers of two neighboring volume elements belonging to the same aggregate are merged into a single index number, until this operation is no longer possible. An index number identifying each connected component of each class is thus obtained, this constituting the final segmentation image.

Applications of the Method According to the Invention

1) Applications Carried Out:
a) Rat Phantom:

"MCAT" Digital Phantom:

In order to validate the method, a digital phantom of a rat was produced on the basis of the "MCAT" phantom [Segars, 2004] and simulated on a Siemens camera of "HR+" type. This phantom's organs, segmented on a X-ray scanner image, are modeled by "NURBS" surfaces. Apart from a smoothing of the contours of the organs, this modeling allows fast calculation of deformation. The rat phantom therefore takes into account the motions due to respiration and heart beats.

These high-frequency periodic motions generate a mixture of kinetics of the moving organs. A volume element of the image, fixed in the reference frame of the camera simulated, therefore contains a mixture of the kinetics of the organs which have passed through it during these two physiological motions.

The filling of the bladder during the examination, a physiological motion which handicaps the segmentation much more than periodic motions, as we saw previously, is not taken into account by the "MCAT" phantom. We have simulated it by a progressive dilation of the zone of the image corresponding to the bladder along the examination simulated. The latter comprises 37 successive images acquired over a duration of one minute each.

Determination of the Physiological Kinetics:

A prior calculation, for each frame, of the probability of each volume element belonging to the various organs makes it possible to rapidly rebuild a noise-free PET image, based on the following equation [Kamasak, 2003]:

$$C_j(t) = \sum_{i=1}^{I} (p_{i,j} \times [Vb_{i,j} \times Ca(t) + (1 - Vb_{i,j}) \times Ct_i(t)]),$$

where $p_{i,j}$ is the probability that volume element j belongs to organ i, Ca(t) is the vascular kinetic, identical for all volume elements j and all pharmaco-organs i, $Ct_i(t)$ is the tissular kinetic of organ i, identical for all volume elements j and $Vb_{i,j}$ is a scalar representing the blood volume ratio in the volume element j of organ i.

Once the arterial kinetic Ca(t) has been determined, $Ct_i(t)$ is calculated as a convolution of the arterial kinetic with a weighted sum of decreasing exponentials [Kamasak, 2003].

$$Ct_i(t) = Ca(t) * \left( \sum_{w=1}^{W} [a_{i,w} \times e^{-t/b_{i,w}}] \right)$$

The parameters $a_{i,w}$ and $b_{i,w}$ are determined randomly for each exponential function w and each pharmaco-organ i.

Projection and Reconstruction:

This "4D" image is then projected analytically, noise-affected and reconstructed by either an analytic, or iterative reconstruction algorithm. The various detection or reconstruction phenomena such as fortuitous coincidences, Compton scattering and "spill-over" are also simulated.

Segmentation and Criterion of Quality of Segmentation:

The segmentation of the image and the comparison of the results with the probabilities of belonging to the various organs makes it possible to establish, once identification i(I) has been carried out between label $I_j$ and the corresponding organ i, a global criterion of quality of segmentation:

$$\frac{1}{J} \times \left[ \sum_{j=1}^{J} \left( \frac{p_{i(I_j),j}}{\max_k (p_{k,j})} \right) \right].$$

This criterion will be equal to 1 for perfect segmentation and to 0 for catastrophic segmentation. We can also define a criterion of detection of the organs, corresponding to the number of organs for which a direct organ-to-organ correspondence is impossible, on account of a merging or of a splitting of two organs in the segmentation image, divided by the number, defined in the phantom, of organs.

b) "PNA" Project:

"PNAs" ("Peptidic nucleic acids") have shown great efficacity in anti-sense strategies for blocking gene expression by degradation of RNAs intracellular messengers. The use of such molecules in animals necessitates knowledge about their in vivo behavior. Little information was available on the pharmacokinetic properties of these molecules. The data available indicated that these compounds were stable in the plasma, excreted in the urine, and that they were captured very little in other organs (non specific fixation).

Consequently, this type of oligonucleotide seemed ideal for developing methods making it possible to modulate their pharmacokinetic parameters in a forecastable manner. The functionalization (chemical modification) of the peptide skeleton of "PNAs" made it possible to synthesize twelve derivatives still possessing their anti-sense activity. These derivatives were marked with fluorine 18 and their pharmacokinetics were analyzed by PET imaging in rats. For each "PNA", four animals were treated by injection simultaneously. By applying the automatic PET image segmentation method to this series of twelve "PNAs" plus a control "PNA", it was possible to automatically isolate the organs and thus to obtain the pharmacokinetic parameters per organ for each type of "PNA". The kinetics obtained automatically showed good agreement with the kinetics obtained by manual segmentation of the organs discernible on the PET image.

This study shows that the pharmacokinetics and pharmacodistributions of oligonucleotides may be greatly modified. These results present a great advance in the development of "drugs" of "PNA" type for in vivo use for therapeutic ends.

2) Envisaged Applications of the Method of the Invention:

The automatic image segmentation method according to the invention using the pharmacokinetic information can be applied advantageously to any study based on a measure localized in space, within an organism, and exhibiting a variation over time. The modalities concerned are in particular nuclear medicine (PET and "SPECT" techniques, in particular), and also functional MRI and optical imaging.

The following applications may in particular be cited.

a) Pharmaco Imaging:

Whole-Body PET Imaging:

The present method of segmentation makes it possible to obtain good segmentation, despite the physiological motions of the subject imaged.

Pharmaco-Imaging without a Priori:

The present method of segmentation requires no prior knowledge about the response of the various organs to the tracer.

In Vivo Sorting of Molecules:

Faced with the capabilities of combinatorial chemistry to generate large banks of molecules, the problem arises of the selection of molecules of interest. This selection may be effected in vitro or as a function of chemical characteristics, of polarity or of geometrical characteristics of the molecule, but there is then nothing to ensure the crossing of the system barriers and the in vivo efficacy of the molecule.

The in vivo bio distribution provides information about the targeting capabilities of the molecule injected into the imaged subject. It therefore becomes possible to select a molecule from a group of molecules of interest. However, the manual processing of the data of a large number of examinations is a lengthy and irksome task, which in fact limits the quantity of molecules tested.

The present method of segmentation makes it possible, through its automatic nature and its speed, to rapidly process a large number of examinations, allowing in vivo sorting whose throughput is henceforth limited by the acquisition of the examinations and not the processing of the data arising from them.

Study of Novel Tracers

The present method requiring no a priori knowledge of the behavior of the tracers—the model applied remains valid for any tracer—, it enables details to be obtained rapidly regarding the pharmacokinetics of a novel tracer, with unknown properties.

Targeting of Organs:

Certain molecules are of interest in vitro on account of their active principle, but do not enter a target organ. They are therefore of no interest in vivo. However, by adding chemical tags that do not modify the active principle of such a "drug", or that encapsulate it in a vector, it becomes possible to modify its targeting capabilities.

Such a molecule thus earmarked generates a family of molecules with active principle assumed identical, but whose pharmacokinetics will be different. The molecules thus generated may undergo in vivo sorting, as described hereinabove, to select those which exhibit the required targeting capabilities.

b) Imaging in Physiology:

c) Detection of Analogy of Response of Organs to a Tracer:

The present method of segmentation does not make it possible to distinguish two pharmaco-organs with identical functionings. In the image resulting from the segmentation procedure, these two organs will have been allocated the same label. It is thus possible to chart analogies between the functionings of two organs.

In a similar manner, certain organs are present in the organism in pairs (eyes, kidneys, lungs). If the segmentation procedure enables them to be dissociated, it is highly probable that their response to the tracer is different, for example on account of the dysfunctioning of one of them.

d) Determination of Models of Kinetics:

Step 40 of defining samples—or even directly step 30 which extracts the model-voxels—makes it possible to estimate the models of kinetics specific to each organ. In the exemplary embodiment given, the models of all the organs, straight lines in the space of kinetics, have a single point of intersection: the arterial kinetic. The latter may therefore theoretically be determined by calculating the intersection of the model-lines in the space of kinetics.

The estimation of these models being biased by the partial volume effect and a relatively small number of samples, the lines will probably not have any point of intersection, but will pass close to the arterial kinetic. The estimation of the models may therefore allow direct estimation of the arterial kinetic or else serve as initialization for a method enabling it to be done.

e) Segmentation Prior to a Reconstruction of the Kinetics of the Structures:

Henceforth counted among the uses of segmentation is the reconstruction of the kinetics in the organism, not volume element by volume element, but organ by organ. Specifically, the signal-to-noise ratio depends on the fineness of the temporal sampling and the spatial resolution. By degrading spatial resolution, it is possible to refine the temporal sampling. Rather than to degrade the spatial resolution in an arbitrary manner, it seems natural to group together the volume elements having an identical response to the tracers.

Rather than to segment anatomical images and to register them on the PET modality in order to determine these groupings, the segmentation procedure proposed makes it possible to dispense with the anatomical modality by using as grouping the pharmaco-organs arising from the segmentation. Specifically, registration between anatomical and functional modality is rendered difficult in the case of the whole body, and the anatomical modality is not even always available.

f) Use of Kinetics Models in Image Reconstruction:

The method of segmentation according to the invention affords access to a kinetic model of each structure present in the image. Access to this model does not necessitate complete segmentation of the image. This kinetic model may have numerous applications, such as for example "4D" reconstruction in PET [Nichols, 2002].

More generally, the time information may be used as a priori, or in the guise of additional information to improve the quality of the images, especially in terms of statistical fluctuation.

g) Recognition of Structures in PET:

The method of segmentation according to the invention enables volume elements belonging to the same pharmaco-organ to be grouped together under the same label. It then remains to recognize the organs corresponding to the various labels. The hierarchical representation proposed here ought to facilitate this recognition step, by charting the merge level making it possible to reveal a specific organ isolated from the others and as a single piece.

h) Verification of the Functional Coherence of an Anatomically Segmented Organ:

The correlation between the anatomical contours of an organ and the identity of the responses of its sub-parts to a given tracer is not ensured—when a tumor is present for example. The procedure proposed makes it possible to automatically separate an organ into sub-parts with distinct responses to the tracer.

i) Time Sequences in Optical Imaging:

Optical imaging makes it possible to obtain anatomical and also functional images. These images exhibit very high spatial and temporal resolution. The method according to the invention makes it possible to segment such images automatically.

j) Static Images:

The present method may be applied to purely "2D" or "3D" images, by employing a suitable model chosen during step 10.

BIBLIOGRAPHIC REFERENCES CITED

Ashburner and coll., A cluster analysis approach for the characterization of dynamic PET data. *Quantification of Brain Function using PET*, pages 301-306, San Diego, Academic Press (1996).

Acton, P. D., Pilowsky, L. S., Kung, H. F., Ell, P. J. Automatic segmentation of dynamic neuroreceptor single-photon emission tomography images using fuzzy clustering. *European Journal of Nuclear Medecine and Molecular Imaging*, Springer-Verlag, Heingelberg, 26(6):581-590 (1999).

Brankov, J. G., Galatsanos, N. P., Yongyi Yang Wernick, M. N., Segmentation of dynamic PET or fMRI images based on a similarity metric. *IEEE Transactions on Nuclear Science*, 50(5):1410-1414 (2003).

Guo, H., Renaut, R., Chen, K., Reiman, E. Clustering huge data sets for parametric PET imaging, *BioSystem* 71, 81-92 (2003).

Frouin, F., Boubacar, P., Frouin, V., De Cesare, A., Todd-Pokropek, A., Merlet, P., Herment, A. 3D regularization and segmentation of factor volumes to process PET H215O myocardial perfusion studies. Functional Imaging and Modeling of the Heart (FIMH'2001). *Lecture Notes in Computer Sciences*, Springer Verlag, Heidelberg, 2230: 91-96 (2001).

Frouin, V., Comtat, C., Reilhac, A., Grégoire, M.-C., Correction of Partial-Volume Effect for PET Striatal Imaging: Fast Implementation and Study of Robustness. *Journal of Nuclear Medicine* 43-12:1715-1726 (2002).

Jain, A. K., Dubes, R. C., Algorithm for Clustering Data. Advanced Reference. Prentice-Hall, Englewood Cliffts, N.J. (1988).

Kimura, Y., Senda, M., Alpert, N. Fast formation of statistically reliable FDG parametric images based on clustering and principal components. *Phys. Med. Biol.* 47(3):455-468 (2002).

Mangin, J.-F., Coulon, O., Frouin V., Robust Brain Segmentation Using Histogram Scale-Space Analysis and Mathematical Morphology. *MICCAI*, Springer Verlag, Heidelberg, LNCS 1496, pp. 1230-1241 (1998).

Minka, T. P., Automatic choice of dimensionality for PCA. *M.I.T. Media Laboratory Perceptual Computing Section Technical Report No* 514 (2000).

Nichols, T. E., Qi, J., Asma, E., Leahy, R. M., Spatiotemporal Reconstruction of List-Mode PET Data. *IEEE Transactions on Medical Imaging*, 21(4):396-404 (2002).

Segars, W. P., Tsui, B. M. W., Frey, E. C., Johnson, G. A., Berr, S. S., Development of a 4D Digital Mouse Phantom for Molecular Imaging Research. *Molecular Imaging and Biology* (2004).

Tipping, M. E., Bishop, C. M., Mixture of probabilistic principal component analyzers. *Neural Computation*, 11 (2):443-482 (1999).

Wong, K.-P., Feng, D., Meikle, S. R., Fulham, M. J. 2001. *IEEE Transactions on Nuclear Science* 49:200-207 (2002)

Zhou, Y., Huang, S.-C., Bergsneider, M., Wong, D. F. A non linear regression with spatial constraint for generation of parametric images in dynamic PET studies. *Journal of Nuclear Medecine* 42 (5), 100.

ANNEX A

Profile of the Kinetics in a Compartmental Model with Four Parameters

Model of Kinetic with a Single Tracer:

The model $M_{i,j}(t)$ of the PET signal within a given volume element j lying within organ i may be written, after correction for radioactive decay:

$$M_{i,j}(t) = ((1-Vb_{i,j}) \times Ct_i(t) + Vb_{i,j} \times Ca(t)) \times D$$

where D is the dose injected and $Vb_{i,j}$ is the blood volume ratio within volume element j of organ i.

When j moves within organ i, $M_{i,j}(t)$ describes a segment of the straight line $Ca(t)Ct_i(t)$ in the space of kinetics.

Model of Kinetic with Several Tracers:

When several tracers $\{Tr_s\}_{1 \leq s \leq S}$ are injected within the organism, the activity obtained within volume element j in the course of time is the sum of the kinetics of the various tracers. If the tissular and plasmatic kinetics depend on the tracer, the plasmatic volume ratio within volume element j is itself independent of s. The model $M_{i,s,j}(t)$ may be written, after correction for radioactive decay:

$$M_{i,s,j}(t) = \sum_{s=1}^{S} [D_s \times ((1-Vb_{i,j}) \times Ct_{i,s}(t) + Vb_{i,j} \times Ca_s(t))]$$

$$M_{i,s,j}(t) = \left((1-Vb_{i,j}) \times \sum_{s=1}^{S} (D_s \times Ct_{i,s}(t)) + Vb_{i,j} \times \sum_{s=1}^{S} (D_s \times Ca_s(t))\right)$$

$M_{i,s,j}(t)$ still belongs to a straight line in the space of kinetics, this time the line passing through $$\sum_{s=1}^{S} (D_s \times Ct_{i,s}(t)) \text{ and } \sum_{s=1}^{S} (D_s \times Ca_s(t)).$$

Partial Volume Effect:

The partial volume effect may be modeled [Frouin, 2002] as a smoothing of the image. The signal $S_j$ measured in the image within a volume element j is therefore a linear combination of the models $M_{i,k}$ of pharmaco-organs of the neighboring volume elements k. Let us consider for greater clarity the case of the injection of a single tracer.

$$S_j(t) = \sum_{k \in Neighbourhood(j)} (\beta_{j,k} \times M_{i(k),k}(t))$$

Within an Organ:

When the neighborhood of j over which the partial volume effect extends contains only organ i, the signal $S_j(t)$ may be written:

$$S_j(t) = \left[\sum_{k \in Neighbourhood(j)} (\beta_{j,k} \times (1-VB_{i,k}))\right] \times$$

$$\sum_{s=1}^{S} (D_s \times Ct_{i,s}(t)) + \left[\sum_{k \in Neighbourhood(j)} [\beta_{j,k} \times Vb_{i,k}]\right] \times \sum_{s=1}^{S} (D_s \times Ca_s(t))$$

$S_j(t)$ still belongs to the line passing through $$\sum_{s=1}^{S} (D_s \times Ct_{i,s}(t)) \text{ and } \sum_{s=1}^{S} (D_s \times Ca_s(t)).$$

At the Boundary of an Organ:

When, conversely, this neighborhood of j contains l (l>1) organs whose models are different, $C_j$ is calculated as a linear combination of the signals each belonging to one of the straight lines $M_{i,j}$. The whole set of signals contained in the neighborhood of j cannot therefore be described by a straight line.

Specifically:

$$S_j(t) = \sum_{i=1}^{l} \left(\left[\sum_{k \in Neighbourhood(j) \cap i} (\beta_{j,k} \times (1-Vb_{i,k}))\right] \times \right.$$

$$\sum_{s=1}^{S} (D_s \times Ct_{i,s}(t)) + \left[\sum_{k \in Neighbourhood(j) \cap i} [\beta_{j,k} \times Vb_{i,k}]\right] \times$$

$$\left. \sum_{s=1}^{S} (D_s \times Ca_s(t))\right)$$

$$S_j(t) = \sum_{i=1}^{l} \left(\left[\sum_{k \in Neighbourhood(j) \cap i} (\beta_{j,k} \times (1-Vb_{i,k}))\right] \times \right.$$

$$\sum_{s=1}^{S} (D_s \times Ct_{i,s}(t))\right) + \left[\sum_{i=1}^{l} \left(\sum_{k \in Neighbourhood(j) \cap i} [\beta_{j,k} \times Vb_{i,k}]\right)\right] \times$$

$$\sum_{s=1}^{S} (D_s \times Ca_s(t))$$

$$S_j(t) = \sum_{i=1}^{l} \left(a_{i,j,k} \times \sum_{s=1}^{S} (D_s \times Ct_{i,s}(t))\right) + b \times \sum_{s=1}^{S} (D_s \times Ca_s(t))$$

The vectors $Ca_s(t)Ct_{i,s}(t)$ not being colinear for $1 \leq i \leq l$, since the models are assumed to be different, $S_j(t)$ therefore does not describe a straight line but a subspace of dimension d such that $1 < d \leq l$.

Physiological Motion:

In the zones in space that are affected by a non periodic physiological motion or one whose period is greater than the duration of acquisition of an image of the series, one in the same volume element j does not contain the same organs for all the images of the series. The analysis of the kinetic from the first instant of acquisition to the last is therefore meaningless. Such is the case in particular in the bladder and the viscera.

Let us consider a zone of the image affected by periodic motion of much lower period than the duration of acquisition. The signal is accumulated over a duration in the course of which a large number of periods are completed. The acquisition time $\Delta t$ for an image may be split up into:

$\Delta t = n \times P + \delta t$, where P is the period of the physiological motion. If $P \ll \Delta t$, we also have $\delta t \ll \Delta t$. If the kinetic of the tracers is assumed to be continuous, the signal recorded over the duration $\delta t$ is negligible compared with the signal recorded over the duration $n \times P$. Hence, more or less, the same physiological sites are observed within a given volume for each image of the series studied. The proof of the linear nature of the model with an organ despite the partial volume effect is readily transposable to the problem of fast periodic physiological motion.

Let k be a unit of volume with center x moving with the structures along a curve $\Omega$ and j a unit of volume fixed in the field of view.

Motion within the Same Organ i:

The signal $S_j(t)$ at volume element j may be written:

$$S_j(t) = \left[ \oint_\Omega (\beta_{j,k(x)} \times (1 - Vb_{i,k(x)})) dx \right] \times \sum_{s=1}^{S} (D_s \times Ct_{i,s}(t)) + \left[ \oint_\Omega (\beta_{j,k(x)} \times Vb_{i,k(x)}) dx \right] \times \sum_{s=1}^{S} (D_s \times Ca_s(t))$$

$S_j(t)$ still belongs to the line passing through $$\sum_{s=1}^{S} (D_s \times Ct_{i,s}(t)) \text{ and } \sum_{s=1}^{S} (D_s \times Ca_s(t)).$$

Motion Passing Through Several Organs:

$$S_j(t) = \sum_{i=1}^{I} \left[ \left( \int_{\Omega \cap i} (\beta_{j,k(x)} \times (1 - Vb_{i,k(x)})) dx \right) \times \sum_{s=1}^{S} (D_s \times Ct_{i,s}(t)) \right] + \sum_{i=1}^{I} \left[ \int_{\Omega \cap i} (\beta_{j,k(x)} \times Vb_{i,k(x)}) dx \right] \times \sum_{s=1}^{S} (D_s \times Ca_s(t))$$

$S_j(t)$ does not therefore describe a straight line, but a subspace of dimension d such that $1 < d \leq I$.

Physiological Motion and Partial Volume Effect:

It may be shown in a known manner that the model with one organ i is retained only if the neighborhood of k over which the partial volume extends, during the entire journey $\Omega$ of k—with center x—due to the periodic physiological motion, is included in i.

Still under the assumption that there do not exist two different organs which are such that their models of kinetics are identical, the signal $S_j(t)$ at volume element j fixed in the field of view belongs to the straight line $Ca(t)Ct_i(t)$ for any j, if and only if the neighborhood of j over which the partial volume effect extends remains included in organ i during the periodic physiological motion.

Conclusion:

If we exclude zones of non periodic or long-period physiological motion, and if we assume that no pairs of organs possess the same kinetic model, the model with one organ i is therefore valid within a volume B, fixed in the frame of reference of the camera, if and only if the neighborhood Neigh(B) of this volume over which the partial volume effect extends remains included in organ i during the period of the physiological motion.

ANNEX B

Choice of the Measure of Local Non Validity of the Model with One Organ

1) Likelihood of the Signal Model Chosen:

If $B_{j,r}$ is included in a pharmaco-organ i, $H_0$: $C_j(t)$ may be written $C_j(t) = \mu_i(t) + \gamma_{i,j} \times e_i(t) + \epsilon_j(t)$ The likelihood of $H_0$ is a good indicator of the validity of the model over $B_{j,r}$. When the ball $B_{j,r}$ is included in an organ, the dimension of the signal is equal to 1. Model selection within the Bayesian framework, if $C_{j,r}$ is the set of kinetics contained in the ball $B_{j,r}$ and K is the number of organs present in $B_{j,r}$, amounts to maximizing:

$$p(C_{j,r}/k) = \int_\theta p(C_{j,r}/\theta) p(\theta/K) d\theta \text{ for } K = 1.$$

In the case of a PCA modeling (principal component analysis) with Gaussian additive noise, the Laplace approximation of the proof $P(C_{j,r}/k)$ for the model with K eigenvectors shows itself [Minka, 2000] to be an excellent indicator of the actual dimension of the model.

The Laplace approximation of the likelihood of the data according to the model with K dimensions may be written:

$$p(\theta) \approx f(\Theta)(2\pi)^{rows(A)/2} |A|^{-1/2}$$

with $\Theta = \underset{\theta}{\mathrm{argmax}}(f(\theta))$, $A = -\left[\dfrac{d^2 \log f(\theta)}{d\theta_i d\theta_j}\right]_{\theta=\Theta}$ and $\theta = (U, \Lambda, v)$.

U is the matrix of eigenvectors of the correlation matrix, $\Lambda$ the matrix of eigenvalues and v an estimate of the variance of the noise and of the signal not reconstructed by the PCA within the ball $B_{i,r}$. Let U',L' and v' be the values of the parameters U, $\Lambda$ and v maximizing $f$.

$$v' = \frac{N \sum_{l=K+1}^{d} \lambda_l}{n(d-k)-2}$$

The diagonal values of $\Lambda$ may be written $$\lambda'_l = \frac{N\lambda_l + \alpha}{N - 1 + \alpha}$$

for $l \leq K$ and $\lambda_i = V$ otherwise, with $\alpha$ representing the magnitude of the a priori.

$$p(C_{j,r}/K) \approx p(U) \left(\prod_{k=1}^{K} \lambda_j\right)^{-N/2} V^{-N(d-k)/2} (2\pi)^{(m+k)/2} |A|^{-1/2} N^{-k/2}$$

Local Maxima of the Likelihood of the Model with One Organ:

Let j be such that the likelihood of the data according to the model of organ i is a maximum on $B_{j,r}$.

j satisfies $p(C_{j,r}/K=1) > p(C_{k,r}/K=1)$ for any k belonging to the neighborhood of j.

After a calculation of the spatial map of the $p(C_{j,r}/K=1)$, the local maxima are extracted. Each local maximum situated in an organ corresponds to a maximum likelihood of the validity of the model. These points are therefore hardly marred by partial volume, in which case the dimension of the model necessary for the characterization of the signal will be greater than 1.

Discussion: This measurement turns out in practise to be extremely noisy and poorly selective of the interior of the organs.

Map of the Number of Organs Present in the Neighborhood:

$$D_j = \underset{K}{\operatorname{argmax}}(p(C_{j,r}/K))$$

is the most likely dimension of the data within $B_{j,r}$. The zones $D_j$ is equal to 1 are zones situated in the interior of the organ.

Discussion: This index exhibits noise points that are impossible to dissociate from the real volume elements j such that $B_{j,r}$ is included in an organ. Moreover, the organs of small size or of elongate shape exhibiting no points that are not marred by the signal of the neighboring pharmaco-organs—on account of the partial volume effect—they are not detected.

2) Local Principal Component Analyses:

Let $\{e_{j,t}(t)\}_{1 \leq t \leq T}$ be the eigenvectors of a principal component analysis (PCA), centered at $\mu_j(t)$, operated on the kinetics of the volume elements included in the ball $B_{j,r}$. Let $\sigma_{j,t}^2$ be the variance of time t of the noise $\epsilon_j(t)$ and $\{\lambda_{j,t}\}_{1 \leq t \leq T}$ the eigenvalues of the PCA.

The mean variance of $\epsilon_j(t)$ may be written:

$$\sigma_j^2 = \frac{1}{T} \times \sum_{t=1}^{T} \sigma_{j,t}^2 = \lambda_j^2, \text{ with } \lambda_j^2 = \frac{1}{T-1} \sum_{l=2}^{T} \lambda_{j,l}^2.$$

Let us consider to begin with the case of a reconstruction by an analytic method. The noise being stationary both in space and in time, its variance is constant: $\sigma_{j,t}^2 = \sigma^2$. Within the organ $$\sigma^2 = \frac{1}{T-1} \sum_{l=2}^{T} \lambda_{j,l}^2.$$

$\lambda_j^2$ therefore seems to be a good indicator of the position of volume element j with respect to the boundaries of the organs.

Specifically, or when volume element j contains, on account of the partial volume effect, the kinetics of several pharmaco-organs, the eigenvalues of the PCA that are not taken into account in modeling the signal contain both pharmaco-kinetic information and noise. We will then have $\sigma^2 < \lambda_j^2$, with $$\lambda_j^2 = \frac{1}{T-1} \sum_{l=2}^{T} \lambda_{j,l}^2.$$

We therefore deduce that $\lambda_j^2/\sigma^2 \sim 1$ when j is in the core of an organ and $\lambda_j^2/\sigma^2 \gg 1$ when j is at the boundary between two organs.

However, this measure does not make it possible to discriminate the points interior to the organism from the exterior points. Specifically, when j is situated outside the organism, the exterior of the organism containing no tracer, j contains only noise, hence $\lambda_j^2/\sigma^2 = 1$.

Likewise, between organs i and o, i exhibiting a strong signal and o a weak signal of the order of the variance of the noise, $\lambda_j^2/\sigma^2$ will be little different from 1.

Mean of the Proportion of Non Reconstructed Signal:

Let us define the following measure of signal-related local inhomogeneity of the kinetics:

$$PNR_j = \frac{1}{N} \times \sum_{\{k/k \in B_{j,r}\}} \left[\frac{\|\varepsilon_{j,k}\|^2}{\|C_k\|^2}\right]$$

Let j be such that $B_{j,r} \subset$ organ i, and m such that $\#(B_{m,r} \cap B_{i,r}) \gg \#(B_{m,r} - B_{m,r} \cap B_{i,r})$ and that $B_{m,r} - B_{m,r} \cap B_{i,r}$ consist of points exterior to the organ, whose kinetics may be modeled by the first K vectors of the PCA calculated on i. Let us assume $\sigma_j \ll \|\mu_j\|^2$:

1) For k such that $k \in B_{m,r} \cap i$, $$\frac{\|\varepsilon_{j,k}\|^2}{\|C_k\|^2} \sim \frac{\sigma_i^2}{\|\mu_i\|^2},$$

while $$\frac{\|\varepsilon_{m,k}\|^2}{\|C_k\|^2} \sim \frac{\lambda_m^2}{\|\mu_i\|^2},$$

with $\lambda_m > \sigma_i$, as we saw earlier.

2) For k such that $k \in B_{m,r} - B_{m,r} \cap i$, $$\frac{\|\varepsilon_{m,k}\|^2}{\|C_k\|^2} \sim 1,$$

since $C_k$ is poorly reconstructed by the PCA characterizing organ i.

3) For k such that $k \in B_{j,r} - B_{m,r} \cap i$, $P_k$ belongs to organ i:

$$\frac{\|\varepsilon_{j,k}\|^2}{\|C_k\|^2} \sim \frac{\sigma_i^2}{\|\mu_i\|^2} << 1.$$

$$PNR_m - PNR_j = \frac{1}{N} \times \left( \sum_{\{k/k \in B_{j,r}\}} \left[\frac{\|\varepsilon_{j,k}\|^2}{\|C_k\|^2}\right] - \sum_{\{k/k \in B_{m,r}\}} \left[\frac{\|\varepsilon_{m,k}\|^2}{\|C_k\|^2}\right] \right)$$

$$PNR_m - PNR_j = \begin{bmatrix} \overbrace{\frac{1}{N} \times \left( \sum_{\{k/k \in B_{j,r} \cap B_{m,r}\}} \left[\frac{\|\varepsilon_{m,k}\|^2}{\|C_k\|^2}\right] - \sum_{\{k/k \in B_{j,r} \cap B_{m,r}\}} \left[\frac{\|\varepsilon_{j,k}\|^2}{\|C_k\|^2}\right] \right)}^{A} + \\ \underbrace{\frac{1}{N} \times \left( \sum_{\{k/k \in B_{m,r} - B_{j,r} \cap B_{m,r}\}} \left[\frac{\|\varepsilon_{m,k}\|^2}{\|C_k\|^2}\right] - \sum_{\{k/k \in B_{j,r} - B_{j,r} \cap B_{m,r}\}} \left[\frac{\|\varepsilon_{j,k}\|^2}{\|C_k\|^2}\right] \right)}_{B} \end{bmatrix}$$

$$A \sim N_{\cap} \times \left( \frac{\lambda_m^2}{\|\mu_i\|^2} - \frac{\sigma_i^2}{\|\mu_i\|^2} \right) > 0.$$

$$B \sim 1 - \frac{\sigma_i^2}{\|\mu_i\|^2} > 0.$$

For any volume element k at the boundary of organ i, and for any j such that $B_{j,r}$ is included in organ i, $PNR_k > PNR_j$. With the hypotheses that $\sigma_j << \|\mu_j\|^2$ and that the organs neighboring the organ i are characterized by kinetics exhibiting a high signal proportion not reconstructed by the model defined on i, there therefore exists a minimum $PNR_j$ of PNR within organ i, such that $B_{j,r}$ is included in organ i.

This measure of inhomogeneity requires the calculation of a PCA for each $B_{j,r}$, but also the calculation of the projection of the kinetic of each volume element included in $B_{j,r}$ onto the first eigenvector of this PCA. However, the criterion being calculated on each volume element included in the organism imaged, this extra calculational cost turns out to be prohibitive.

Relative Variance of the Residuals:

Employing the approximation that within and on the boundary of an organ, $\|C_k\|^2 \sim \|\mu_j\|^2$, let us define the following measure of signal-related local inhomogeneity of the kinetics:

$IR_j = \lambda_j^2 / \|\mu_j\|^2$, where $\mu_j$ is the mean of the signal over the ball $B_{j,r}$ included in the organ, and $$\lambda_j^2 = \frac{1}{T-1} \sum_{t=2}^{T} \lambda_{j,t}^2.$$

$\lambda_j^2$ is the variance of the signal not reconstructed by a PCA operated on the kinetics of the volume elements belonging to the ball $B_{j,r}$ centered at j and of radius r, only the first K eigenvectors of which have been retained.

Non Reconstructed Relative Variance Corrected for Iterative Reconstructions:

In the case of an iterative reconstruction with a fixed number of iterations for each image of the reconstructed sequence, the variance of the noise $\sigma_j^2(t)$ at the volume element j and at the instant t may be written:

$\sigma_j^2(t) = \alpha^2 \times S_j(t)/\Delta t.$ $\sigma_j^2(t)$ is non stationary, both from a spatial and temporal point of view, since it is proportional to the signal. In order to circumvent the contribution of the signal to the variance of the noise, precluding any comparison of variance of noise between voxels, we shall study not $\sigma_j^2(t)$, but $\alpha^2 = \sigma_j(t)^2/S_j(t) \times \Delta_t$. Specifically, $\alpha^2$ is a quantity independent of the signal of the duration of acquisition of the images of the sequence, hence stationary in space and time.

If we assume a continuous and weak variation of the signal in space, $S_{j,k}(t)$, for $k \in B_{j,r}$, can be approximated by the mean kinetic $\mu_{j,t}$ within the ball $B_{j,r}$. Likewise, $S'_{j,k}(t) = S_{j,k}(t) \times \Delta_t$ may be approximated by $\mu'_j(t)$ the mean of the kinetics $C'_k t$) within the ball $B_{j,r}$.

Consider the principal component analysis ($\mu'_j(t)$, $\{\lambda'_{j,t}\}$, $\{e'_{j,t}(t)\}$) calculated on the kinetics $C''_{j,k}(t) = C'_k(t)/\sqrt{\mu'_i(t)} = C_k(t) \times \Delta_t / \sqrt{\mu'_i(t)}$.

$C''_{j,k}(t) = S_{j,k}(t) \times \Delta_t / \sqrt{\mu'_i(t)} + N(0, \alpha'^2) = S''_{j,k}(t) + N(0, \alpha'^2)$, with $\alpha' \approx \alpha$, stationary in space. When $B_{j,r}$ is included in an organ i, $S''_{j,k}(t) = M''_{j,k}(t)$ and describes a straight line in the space of kinetics when j moves within i.

The criterion of non reconstructed relative variance becomes $$\Gamma'_{V_j} = \frac{\lambda_j'^2}{\|\mu_j\|^2},$$

which measures the validity of the model with one organ within the ball $B_{j,r}$.

ANNEX C

Variations of the Exemplary Embodiment in the Case of Images Reconstructed by an Iterative Algorithm In the case of an iterative algorithm, the variance of the noise is correlated with the signal. In order to be able to compare two indices based on a measure of the error of reconstruction by the pharmaco-organ kinetic model, it therefore seems essential to correct for this influence of the signal whenever possible.

In the case of an iterative reconstruction with a fixed number of iterations for each image of the reconstructed sequence, the variance of the noise $\sigma_j^2(t)$ at the volume element j and at the instant t may be written:

$$\sigma_j^2(t) = \alpha^2 \times S_j(t)/\Delta_t.$$

$\sigma_j^2(t)$ is non stationary, both from a spatial and temporal point of view, since it is proportional to the signal. In order to circumvent the contribution of the signal to the variance of the noise, precluding any comparison of variance of noise between voxels, we shall study not $\sigma_j^2(t)$, but $\alpha^2 = \sigma_j(t)^2/S_j(t) \times \Delta_t$. Specifically, $\alpha^2$ is a quantity independent of the signal of the duration of acquisition of the images of the sequence, hence stationary in space and time.

Indicator of the Interior of the Organs:

If we assume a continuous and weak variation of the signal in space, $S_{j,k}(t)$, for $k \in B_{j,r}$, can be approximated by the mean kinetic $\mu_{j,t}$ within the ball $B_{j,r}$. Likewise, $S'_{j,k}(t) = S_{j,k}(t) \times \Delta_t$ may be approximated by $\mu'_j(t)$, the mean of the kinetics $C'_k(t)$ within the ball $B_{j,r}$.

Consider the principal component analysis $(\mu'_j(t), \{\lambda'_{j,i}\}, \{e'_{j,i}(t)\})$ calculated on the kinetics $C''_{i,k}(t) = C'_k(t)/\sqrt{\mu'_i(t)} = C_k(t) \times \Delta_t / \sqrt{\mu'_i(t)}$.

$C''_{i,k}(t) = S_{j,k}(t) \times \Delta_t / \sqrt{\mu'_i(t)} + N(0, \alpha'^2) = S''_{j,k}(t) + N(0, \alpha'^2)$, with $\alpha' \approx \alpha$, stationary in space. When $B_{j,r}$ is included in an organ i, $S''_{j,k}(t) = M''_{i,k}(t)$ and describes a straight line in the space of kinetics when j moves within i.

The criterion of non reconstructed relative variance becomes $$\Gamma'_{v_j} = \frac{\lambda_j'^2}{\|\mu_j\|^2},$$

which measures the validity of the model with one organ within the ball $B_{j,r}$.

Optimization of the Samples:

The non reconstructed proportion of signal calculated on $B_{j,r}$ must be corrected for the influence of the signal on the noise. It becomes $$p''_{j,k} = \frac{\sum_{t=1}^{T} (|\varepsilon'_{j,k}(t)|^2 / S'_{j,k}(t))}{\|C'_k\|^2},$$

where $S'_{j,k}(t)$ is the signal estimated at k as the reconstruction of $C'_k(t)$ by the model with one organ.

$S'_{j,k}(t)$ may be written as $S'_{j,k}(t) = \mu'_j(t) - (e'_{j,l} \cdot C'_k) \times e'_{j,1} \cdot \mu'_j(t)$ is the mean of a kinetics $C'_k(t)$ within the ball $B_{j,r}$ and $e'_{j,1}$ the eigenvector associated with the first eigenvalue of a PCA calculated on the kinetics $C'_k(t)$ within $B_{j,r}$ and centered at $\mu'_j(t)$.

Ranking of the Kinetics:

Consider the model $M''_{i,j}$ defined on the kinetics $C''_{i,j}(t) = C'_j(t)/\sqrt{\mu'_i(t)} = C_j(t) \times \Delta_t / \sqrt{\mu'_i(t)}$ within sample i. $M''_{i,j}$ still describes a straight line in the space of kinetics when j varies within i. The mean reconstruction error within sample i of the kinetic $C''_j(t)$ by the model $M''_{i,j}$ follows a stationary law for j belonging to i.

Once the models $M''_{i,j}$ have been calculated on the basis of the kinetics $C''_{i,j}$ within each sample, the segmentation of the image amounts of finding, for any volume element k, the sample i which minimizes $\|C''_{i,k} - M''_{i,k}\|^2$.

The label o is therefore allocated to volume element k such that:

$$o = \arg\min_i \|C''_{i,k} - M''_{i,k}\|^2.$$

Merging of the Samples:

The variance of the noise associated with the kinetics $C''_{i,j}(t) = C_j(t) \times \Delta_t / \sqrt{\mu'_i(t)}$, for volume element j included in sample i, and equal to $\alpha'^2$, stationary in space and also in time.

Let $$\lambda''^2_i = \frac{1}{T-1} \sum_{i=2}^{T} \lambda''^2_{i,i}$$

be the mean of the T−1 smallest eigenvalues of a PCA calculated on the kinetics $C''_{i,k}(t)$ within sample i. $\alpha'^2$ may be estimated as the mean of the $\lambda''^2_i$ over the samples:

$$\alpha'^2 = \frac{1}{I} \sum_{i=2}^{I} \lambda''^2_i.$$

The cost function for merging two samples a and b becomes:

$$C_{a,b} = \beta \times \max \left[ \frac{1}{N} \times \sum_{k \in a} \frac{\|\varepsilon''_{b,k}\|^2}{\alpha'^2}, \frac{1}{N} \times \sum_{k \in b} \frac{\|\varepsilon''_{a,k}\|^2}{\alpha'^2} \right] +$$

$$\delta \times (1 - \min[\|\mu_a\|_\infty / \|\mu_b\|_\infty, \|\mu_b\|_\infty / \|\mu_a\|_\infty]) +$$

$$\gamma \times \left(1 - \min\left[\frac{t\max_b}{t\max_a}, \frac{t\max_a}{t\max_b}\right]\right)$$

The invention claimed is:

1. A method of segmenting a starting image or sequence of tridimensional images based on voxels for obtaining a tridimensional segmentation image comprising a partition into regions of interest, said image or sequence of images comprising measurements, for each voxel and in a course of n time intervals ($n \geq 1$), of a real evolution of a signal representative of at least one variable of physical, chemical or biological type of said image or sequence, which comprises the following steps:

a) modeling (10) of the signal comprising a definition of a parametric model of spatio-temporal evolution of said signal, this model comprising sets of homogeneous parameters so that said sets are respectively specific to structures corresponding to said regions of interest and that each set of parameters is independent of spatial coordinates in a corresponding structure;

b) extracting (30) of samples of voxels so that said samples are respectively included in said structures, this extraction comprising:
   (i) calculating, for each voxel of said starting image or sequence of images or else of a zone of interest of the latter, a criterion of validity of a hypothesis according to which said model of evolution of said variable within a neighborhood of this voxel is specific to one and only one of said structures,
   (ii) extracting of model-voxels which are defined as realizing a local maxima of said criterion,
   (iii) a defining, for each model-voxel, one of said samples of voxels included in said corresponding structure, in such a way that this sample exhibits an evolution of said variable which complies with that of the model of the structure to which said model-voxel belongs, then
   (iv) estimating, on each sample thus defined, the parameters of said model of evolution of the structure in which said sample is included; then c) merging of said samples grouping together the samples whose evolution model is specific to the same structure, said merging following, preceding or including a classification of all the voxels of said image or sequence of images or of a zone of interest of the latter by aggregation with a group of samples, in such a manner that a maximum similarity exists between the evolution of said variable for these voxels and the evolution of said model characterizing this group of samples, said segmenting obtained by the merging step.

2. The segmentation method as claimed in claim 1, wherein it is granted that there exists in each starting image of said sequence a partition of the space into a finite number of said structures, which are each connected and each exhibit within them a homogeneous behavior in response to a phenomenon studied of which the evolution of said variable is representative.

3. The segmentation method as claimed in claim 2, wherein the number of said structures is determined a posteriori.

4. The segmentation method as claimed in claim 1, wherein said model furthermore comprises heterogeneous parameters dependent on the spatial coordinates of the voxels within one and the same structure, and wherein it is granted for step a) that said homogeneous and heterogeneous parameters can be estimated on one or more volume elements included in this same structure.

5. The segmentation method as claimed in claim 4, wherein it is furthermore granted for step a) that said structures together exhibit different responses to a phenomenon studied of which the evolution of said variable is representative, unless they are not connected.

6. The segmentation method as claimed in claim 5, wherein it is furthermore granted for step a) that the noise, which is inherent in said measurements and which is due to the mode of acquisition of said sequence of starting and segmentation images, is additive.

7. The segmentation method as claimed in claim 6 wherein for step a) the following two constraints are furthermore fixed, so as to take into account local mixtures of various temporal evolutions of said signal:
   (i) if the totality of the voxels which are neighbors of a voxel and which contribute to the evolution of said variable relating to this voxel is included in the same structure, then said corresponding signal is a realization of the model of this structure, and
   (ii) said set of homogeneous parameters for these neighbor voxels is the same as that of said model specific to this structure.

8. The segmentation method as claimed in claim 2, wherein, in the case where said starting image or sequence of images is obtained by an imaging technique by tracer injection, said model used in step a) is a compartmental model of type with one or more independent tracers and with several compartments, such as biological compartments.

9. The segmentation method as claimed in claim 1, wherein step b) of extraction of the model-voxels comprises a prior selection, in a space with n dimensions ($n \geq 1$) corresponding to said starting image or sequence of images, of model-voxels so that each of said structures of interest contains at its heart at least one model-voxel as well as the neighborhood of the latter.

10. The segmentation method as claimed in claim 9, wherein step b) comprises, following said prior selection, the definition of a metric designed to define the distances in said space and said local extraction criterion.

11. The segmentation method as claimed in claim 9, wherein it is granted in step b) that for any structure to be segmented, there exists a voxel whose neighborhood is included within the corresponding region of interest.

12. The segmentation method as claimed in claim 1, wherein step b) comprises:
   a determination, for each structure of interest, of a sample of member voxels belonging to this structure, this membership being determined by a similitude of the evolution of said variable with the model relating to this structure, then
   an estimation, for each sample, of the homogeneous parameters of the model which correspond to said structure.

13. The segmentation method as claimed in claim 1, wherein it furthermore comprises a presegmentation step (20) which is implemented before or after step a) and which consists in separating said starting images into a first part containing said structures of interest and into a second part corresponding to an image background excluded from the segmentation.

14. The segmentation method as claimed in claim 1, wherein step c) of merging (50*a*) and of classification (50*a*) comprises a merging of said samples corresponding to one and the same structure of interest, before or after said classification of the voxels.

15. The segmentation method as claimed in claim 9, wherein the merging of said samples corresponding to one and the same structure of interest is operated by a hierarchical ascending classification.

16. The segmentation method as claimed in claim 1, wherein it furthermore comprises a step of optimization (40) of the samples which is implemented following step b) and before step c) and which consists in seeking, for each sample, a geometric, parametric or free form which minimizes within it the signal of structures other than that whose model-voxel has been extracted.

17. The segmentation method as claimed in claim 1, wherein it furthermore comprises, following step c), a step of separation (70) of the nonconnected structures which exhibit similar evolutions of said variable.

18. The segmentation method as claimed in claim 17, wherein it furthermore comprises a step (60) of hierarchical representation of said regions of interest obtained which is implemented following step c) and before said step of separation of the nonconnected structures.

19. The segmentation method as claimed in claim 1, wherein it excludes the boundary of each structure from the extraction of said samples implemented in step b).

20. The segmentation method as claimed in claim 1, wherein said image or sequence of images is obtained by an imaging technique chosen from the group consisting of positon emission tomography, magnetic resonance imaging, photon emission tomography, optical imagings, X-ray scanner, histological imaging, autoradiographic imaging, satellite imaging and photographic imaging.

21. The segmentation method as claimed in claim 1, wherein said image or sequence of images is obtained by the technique of positon emission tomography.

22. The segmentation method as claimed in claim 21, wherein in step b), local principal component analyses in a space with n dimensions are implemented to determine, as a function of the eigenvalues and of the eigenvectors obtained, the voxels which exhibit a similar temporal evolution of said variable.

23. The segmentation method as claimed in claim 1, wherein said starting images are images of a whole organism, said segmentation method segmenting said organism according to a partition into pharmaco-organs.

24. The segmentation method as claimed in claim 23, wherein said body is imbued with physiological motions either of periodic type, whose period is reduced in comparison with the duration of acquisition of one of the starting images of said sequence, or of nonperiodic type.

25. The segmentation method as claimed in claim 23 wherein said variable represents the radioactive concentration at a given instant $t_0$ to $t_n$ of at least one marked active principle injected into said organism, the whole set of voxels inside each pharmaco-organ exhibiting pharmacological kinetics of distribution of said active principle which are similar.

* * * * *